(12) United States Patent
Sung et al.

(10) Patent No.: US 7,348,030 B1
(45) Date of Patent: Mar. 25, 2008

(54) NANOPARTICLES FOR TARGETING HEPATOMA CELLS

(76) Inventors: Hsing-Wen Sung, 7F, No. 15, Alley 7, Lane 298, Section 2, Kuang-Fu Road, Hsinchu, Taiwan (TW) 300; Hsiang-Fa Liang, 1F, No. 1, Lane 400, Thongjheng Road, Shindian City, Taiwan (TW) 23148; Hosheng Tu, 15 Riez, Newport Beach, CA (US) 92657

( * ) Notice: Subject to any disclaimer, the term of this patent is extended or adjusted under 35 U.S.C. 154(b) by 199 days.

(21) Appl. No.: 11/267,848

(22) Filed: Nov. 4, 2005

Related U.S. Application Data

(63) Continuation-in-part of application No. 10/958,864, filed on Oct. 5, 2004.

(60) Provisional application No. 60/704,561, filed on Aug. 2, 2005.

(51) Int. Cl.
*A61K 9/16* (2006.01)
*A61K 9/14* (2006.01)
*A01N 43/04* (2006.01)

(52) U.S. Cl. .................. 424/491; 424/497; 514/55

(58) Field of Classification Search .................. 514/55; 424/491, 497
See application file for complete search history.

(56) References Cited

U.S. PATENT DOCUMENTS 6,623,729 B2   9/2003   Park et al.

OTHER PUBLICATIONS

Li C Poly(L-glutamic acid)-anticancer drug conjugates, Adv Drug Deliver Rev 2002;54695-713.
Na K et al. Self-assembled hydrogel nanoparticles from curdlan derivatives, J Control Release 2000;69:225-236.
Saul JM et al. Controlled targeting of liposomal doxorubicin via the folate receptor in vitro, J Control Release 2003; 92:49-67.
Liang HC et al. Genipin-crosslinked gelatin microspheres as a drug carrier for intramuscular administration, J Biomed Mater Res 2003; 65A:271-282.
Na K et al. Self-assembled nanoparticles of hydrophobically-modified polysaccharide bearing vitamin H as a targeted anti-cancer drug delivery system, Eur J Pharm Sci 2003;18:165-173.
Liang HF et al, Preparation of nanoparticles composed of poly(gamma-glutamic acid)-poly(lactide) block copolymers and evaluation of their uptake by HepG2 cells, J Control Release 2005;105:213-225.
Richard A et al. Poly(glutamic acid) for biomedical applications, Crit Rev Biotechnol 2001;21:219-232.
Prodhomme EJF et al. Multivalent conjugates of poly-gamma-D-glutamic acid from *Bascillus licheniformis* with antibody F(ab') and glycopeptide ligands, Bioconjug Chem 2003;14:1148-1155.
Rao S et al. Characterization of Taxol binding site on the microtubule, 2-(M-Azidobenzoyl) Taxol photolabels a peptide (amino acids 217-231) of beta-tubulin, J Biol Chem 1995;270:20235-20238.
Gagandeep S et al. Paclitaxel shows cytotoxic activity in human hepatocellular carcinoma cell lines, Cancer Lett 1999;136:109-118.
Jordan MA et al. Mitotic block induced in HeLa cells by low concentrations of paclitaxel results in abnormal mitotic exit and apoptotic cell death, Cancer Res 1996;56:816-825.
Lee IH et al. Stable paclitaxel formulations in oily contrast medium, J Control Release 2005;102:415-425.
Lin HL et al. Comparison of 2-methoxyestradiol-induced, docetaxel-induced, and paclitaxel-induced apoptosis in hepatoma cells and its correlation with reactive oxygen species, Cancer 2000;89:983-994.
Kang TH et al. Antiproliferative effect of alkaloids from *Sedum sarmentosum* on murine and human hepatoma cell line, J Ethnopharmacol 2000;70:177-182.
Yoon SH et al. Production of poly-gamma-glutamic acid by fed-batch culture of *Bascillus licheniformis*, Biotechnol Lett 2000;22:585-588.
Troy FA, Chemistry and biosynthesis of the poly(gamma-D-glutamyl) capsule in *Bascillus licheniformis* II. Characterization and structural properties of the enzymatically synthesized polymer, J Biol Chem 1973;248:316-324.
van Dijk-Wolthuis WNE et al. A new class of polymerizable destrans with hydrolysable groups: Hydroxyethyl methacrylated dextran with and without oligolactate spacer, Polymer 1997;38:6235-6242.
Gref R et al. Stealth corona-core nanoparticles surface modified by polyethylene glycol: Influences of the corona and of the core composition on phagocytic uptake and plasma protein adsorption, Colloid Surface B 2000;18:301-313.
Dong Y et al. Methoxy poly(ethylene glycol)-poly(lactide) nanoparticles for controlled delivery of anticancer drugs, Biomaterials 2004;25:2843-2849.
Zhang L et al. Camptothecin derivative-loaded poly(caprolactone-colactide)-b-PEG-b-poly(caprolactone-co-lactide) nanoparticles and their biodistribution in mice, J Control Release 2004;96:135-148.
Sung HW et al. Crosslinking of biological tissue using genipin and/or carbodiimide, J Biomed Mat Res 2003;64A:427-438.
Liang HC et al. Crosslinking structures of gelatin hydrogels crosslinked with genipin or a water-soluble carbodiimide, J Appl Polym Sci 2004;91:4017-4026.
David A et al. Enhanced biorecognition and internalization of HPMA copolymers containing multi- or multivalent carbohydrate side-chains by human hepatocarcinoma cells, Bioconjug Chem 2001;12:890-899.
Chen CN et al. Feasibility study using a natural compound (reuterin) produced by *Lactobacillus reuterin* in sterilizing and crosslinking biological tissues, J Biomed Mater Res 2002;61:360-369.
Saito T et al. The effect of cell cycle on GFPuv gene expression in the baculovirus expression system, J Biotechnol 2002;93:121-129.
Hashida M et al. Targeted delivery of plasmid DNA complexed with galactosylated poly(L-lysine), J Control Release 1998;53:301-310.
Litzinger DC et al. Effect of liposome size on the circulation time and intraorgan distribution of amphipathic poly(ethylene glycol)-containing liposomes, Biochim Biophys Acta 1994;1190:99-107.
Maeda H et al. Tumoritropic and lymphotropic principles of macromolecular drugs, Crit Rev Ther Drug Carrier Syst 1989;6:193-210.

(Continued)

*Primary Examiner*—Maryam Monshipouri

(57) ABSTRACT

The nanoparticles composed of γ-PGA-PLA block copolymers that are conjugated with galactosamine as a potential drug delivery system and loaded with anticancer drugs for treating liver cancers.

20 Claims, 24 Drawing Sheets

OTHER PUBLICATIONS

Wakebayashi D et al. Lactose-conjugated polyion complex micelles incorporating plasmid DNA as a taragetable gene vector system: their preparation and gene transfering efficiency against cultured HepG2 cells, J Control Release 2004;95:653-664.

Ward CM et al. Systemic circulation of poly(L-lysine)/DNA vectors is influenced by polycation molecular weight and type of DNA: differential circulation in mice and rats and the implications for human gene delivery, Blood 2001;97:2221-2229.

Lee SC et al. Polymeric micelles of poly(2-ethyl-2-oxazoline)-block-poly (episilon-caprolactone) copolymer as a carrier for paclitaxel, J Control Release 2003;89:437-446.

Gref R et al. Biodegradable long-circulating polymeric nenoparticles, Science 1994;263:1600-1603.

Han JH et al. Enhanced hepatocyte uptake and liver targeting of methotrexate using galactosylated albumin as a carrier, Int J Pharm 1999;188:39-47.

Chao Y et al. Phase II and pharmacokinetic study of paclitaxel therapy for unresectable hepatocellular carcinoma patients, Br J Cancer 1998;78:34-39.

Yoon CJ et al. Transcatheter arterial chemoembolization with paclitaxel-lipiodol solution in rabbit VX2 liver tumor, Radiology 2003;229:126-131.

Fuchs J et al. Paclitaxel: an effective antineoplastic agent in the treatment of xenotransplanted hepatoblastoma, Med Pediatr Oncol 1999;32:209-215.

Yuan JH et al. Growth-inhibiting effects of Taxol on human liver cancer in vitro and in nude mice, World J Gastroenterol 2000;6:210-215.

Matsumura Y et al. A new concept for macromolecular therapeutics in cancer chemotherapy: nechanism of tumoritropic accumulation of proteins and the antitumor agent smances, Cancer Res 1986;46:6387-6392.

Hashida M et al. Design of polymeric prodrugs of prostaglandin E1 having galactose residue for hepatocyte targeting, J Control Release 1999;62:253-262.

Son YJ et al. Biodistribution and anti-tumor efficiency of doxorubicin loaded glycol-chitosan nanoaggregates by EPR effect J Control Release 2003;91:135-145.

Kim SC et al. In vitro evaluation of polymeric micellar paclitaxel formulation:toxicity and efficacy, J Control Release 2001;72:191-202.

Garrec DL et al. Poly(N-vinylpyrrolidone)-block-poly(D,L-lactide) as a new polymeric solubilizer for hydrophobic anticancer drugs, J Control Release 2004;99:83-101.

(a)

(b)

(a)

(b)

(a)

(b)

(a)

(b)

NANOPARTICLES FOR TARGETING HEPATOMA CELLS

CROSS-REFERENCE TO RELATED APPLICATIONS

This application is a continuation-in-part application of U.S. patent application Ser. No. 10/958,864 filed Oct. 5, 2004, entitled "Nanoparticles for Targeting Hepatoma Cells," pending the entire contents of the co-pending application are incorporated herein by reference. The application also claims the priority benefits of U.S. Provisional Application No. 60/704,561 filed Aug. 2, 2005, entitled "Nanoparticles for Targeting Hepatoma Cells," The entireties of the priority document are hereby incorporated by reference.

FIELD OF THE INVENTION

The present invention is related to nanoparticles composed of poly(γ-glutamic acid)-poly(lactide) block copolymers as a target drug delivery system, more particularly, the invention is related to nanoparticles loaded with bioactive agents and their uptake by HepG2 cells.

BACKGROUND OF THE INVENTION

Chemotherapy for cancers is usually limited by the toxicity of drugs to normal tissues. Additionally, short circulation half-life in plasma, limited aqueous solubility, and non-selectivity are usually encountered by most of the currently available anticancer drugs and thus restrict their therapeutic efficacy (Adv. Drug Deliver. Rev. 2002; 54:695-713). To reduce the toxicity and increase the therapeutic efficacy of anticancer drugs, various drug carriers, such as soluble polymers, polymeric nanoparticles, liposomes, and microspheres have been investigated (J. Control. Release 2000; 69:225-236; J. Control. Release 2003; 92:49-67; J. Biomed. Mater. Res. 2003;65A:271-282). The biomedical and pharmaceutical applications of self-assembled nanoparticles have recently attracted extensive attentions (Eur. J. Pharm. Sci. 2003; 18:165-173). The self-assembled nanoparticles are composed of a hydrophobic inner core and a hydrophilic outer shell. Core-forming hydrophobic block may affect the drug loading capacity and its release kinetics as a result of hydrophobic interactions between drugs and polymers. In contrast, the hydrophilic shell-forming block determines surface properties of the nanoparticles and influences interactions between the surrounding environments and the nanoparticles (Biomaterials 2003; 24:2053-2059).

Nanoparticles may be delivered to specific sites by size-dependant passive targeting or by active targeting (Cancer Res. 1986; 46:6387-6392; J. Control. Release 1999; 62:253-262). To obtain a high degree of selectivity to a specific organ and to enhance the uptake of drug-loaded nanoparticles into the target cells, active targeting has been attempted by many investigators. Liver has been one of the most desirable target organs in the body due to various liver-related metabolic and infectious diseases and cancers (Int. J. Pharm. 1999; 188:39-47). The asialoglycoprotein (ASGP) receptor is known to be present on hepatocytes and several human hepatoma cell lines (Adv. Drug Deliver. Rev. 1989; 4:49-63). Therefore, liver targeting might be achieved by designing drug delivery systems conjugated with a ligand that can bind to the ASGP receptors.

Poly(lactide) (PLA), poly(ε-caprolactone) (PCL), poly(β-benzyl L-aspartate) (PLBA), and poly(γ-benzyl L-glutamate) (PLBG) have been used mostly for the core-forming hydrophobic segment of nanoparticles (J. Control. Release 2004; 94:323-335). On the other hand, poly(ethylene oxide) (PEO), a non-toxic and highly hydrated polymer, has been used as the outer shell segment of nanoparticles because of its superior biocompatibility (J. Control. Release 2004; 94:323-335). In the present invention, PLA was used for the hydrophobic segment of the block copolymer, while a natural compound [poly(γ-glutamic acid), γ-PGA], produced as capsular substance or as slime by members of the genus *Bacillus*, was used as the hydrophilic segment (Crit. Rev. Biotechnol. 2001; 21:219-232).

γ-PGA is unique in that it is composed of naturally occurring L-glutamic acid linked together through amide bonds rather than a nondegradable C—C backbone such as PEO. It was reported that this naturally occurring γ-PGA is a water-soluble, biodegradable, and non-toxic polymer (Crit. Rev. Biotechnol. 2001; 21:219-232). A related, but structurally different, polymer poly(α-glutamic acid), (α-PGA) is usually synthesized from poly(γ-benzyl-L-glutamate) by removing the benzyl protecting group with the use of hydrogen bromide (Adv. Drug Deliver. Rev. 2002; 54:695-713). Li et al. conjugated paclitaxel onto α-PGA via covalent bonding to form a new drug formulation (Cancer Res. 1998; 58:2404-2409). Their pre-clinical data suggested that the uptake of α-PGA-paclitaxel by tumor cells was about 5-fold greater than that of paclitaxel. Additionally, α-PGA-paclitaxel had a significantly longer circulation half-life in plasma than paclitaxel (Adv. Drug Deliver. Rev. 2002; 54:695-713).

Some aspects of the invention relate to developing novel self-assembled nanoparticles composed of γ-PGA-PLA block copolymers. Physicochemical characteristics of the prepared nanoparticles are examined by dynamic light scattering, transmission electron microscopy, atomic force microscopy, and fluorescence spectroscopy. For the potential of targeting liver cancer cells, the prepared nanoparticles are further conjugated with galactosamine. Hashida et al. reported using α-PGA as a polymeric backbone and galactose moiety as a ligand to target hepatocytes (J. Control. Release 1999; 62:253-262). Their in vivo results indicated that the galactosylated α-PGA had a remarkable targeting ability to hepatocytes and degradation of α-PGA was observed in the liver. The internalization efficiency of the prepared nanoparticles with or without galactosamine conjugated into HepG2 cells (a liver cancer cell line) was examined in vitro using a confocal laser scanning microscope.

Liver cancer is a common lethal disease in Asia (Br J Cancer 1998; 78:34-39). It is also the ninth leading cause of cancer deaths in the United States (Cancer Lett. 1999; 136:109-118). It is known that chemotherapy for cancers is usually limited by the toxicity of drugs to normal tissues (Adv. Drug Deliver. Rev. 2002; 54:695-713). The self-assembled nanoparticles, composed of amphiphilic block copolymers, have a hydrophobic inner core and a hydrophilic outer shell. In a co-pending application U.S. Ser. No. 10/958,864, filed Oct. 5, 2004, it is disclosed that poly(γ-glutamic acid) (γ-PGA) and poly(lactide) (PLA) are used to synthesize amphiphilic block copolymers via a simple coupling reaction between γ-PGA and PLA to prepare a novel type of self-assembled nanoparticles (J. Control. Release 2005; 105:213-225). No aggregation or precipitation of the nanoparticles was observed during storage for up to 1 month, because of the electrostatic repulsion between the negatively charged nanoparticles (J. Control. Release 2005; 105:213-225). γ-PGA, produced by certain *Bacillus* species, is a naturally occurring anionic homo-polyamide that is made of L-glutamic acid units connected by amide linkages between α-amino and γ-carboxylic acid groups (Crit. Rev. Biotechnol. 2001; 21:219-232). Because of its water-solubility, biodegradability, edibility, and non-toxicity toward humans, several applications of γ-PGA in food, cosmetics, and medicine have been investigated in the past few years.

It is one object of the present invention to provide paclitaxel-loaded formulations using the aforementioned nanoparticles composed of amphiphilic γ-PGA-PLA block copolymers for the treatment of liver cancers. For the potential of targeting liver cancer cells, galactosamine was further conjugated on the prepared nanoparticles as a targeting moiety. Paclitaxel is one of the most active anticancer drugs introduced in cancer chemotherapy (Radiology 2003; 229:126-131). However, the hydrophobicity of paclitaxel causes great difficulties in preparing formulations. Many research groups and pharmaceutical companies have endeavored to develop better and improved paclitaxel formulations suitable for different applications (J. Control. Release 2005; 102:415-425). Even though paclitaxel is prescribed mainly to treat breast and ovarian cancers, it is known that paclitaxel can kill effectively various cancer cells including hepatoma cells (Cancer 2000; 89:983-994, J. Ethnopharmacol. 2000; 70:177-182). Additionally, it was reported that paclitaxel significantly inhibits the growth of human hepatoma tumors induced in nude mice by intravenous (i.v.) or intraperitoneal (i.p.) administration (Med Pediatr Oncol 1999; 32:209-215, World J Gastroenterol 2000; 6:210-215).

Owing to its unique structure, paclitaxel readily enters mammalian cells and preferentially binds to tubulin in polymerized microtubules (J. Biol. Chem. 1995; 270:20235-20238). This binding stabilizes microtubules and greatly interferes with microtubular reorganization necessary, among other factors, for spindle formation and cell division (Cancer Lett. 1999; 136:109-118). Thus, exposure of susceptible cells to paclitaxel has been shown to initially cause arrest in the G2/M phase and finally to cell death through apoptotic mechanisms (Cancer Res. 1996; 56:816-825).

There is, therefore, a clinical need for providing nanoparticles composed of γ-PGA-PLA block copolymers conjugated with galactosamine and a bioactive agent as a drug delivery system for the treatment of liver cancers.

SUMMARY OF THE INVENTION

Some aspects of the invention relate to a process for preparing self-assembled nanoparticles using poly(γ-glutamic acid) (γ-PGA) and poly(lactide) (PLA) to synthesize block copolymers via a simple coupling reaction between γ-PGA and PLA. In a further embodiment for targeting liver cancer cells, galactosamine is further conjugated on the prepared nanoparticles as a targeting moiety. γ-PGA, a water-soluble, biodegradable, and non-toxic compound, was produced by microbial fermentation (*B. licheniformis*, ATCC 9945a) and then was hydrolyzed. The hydrolyzed γ-PGA with a molecular weight of 4 kDa and a polydispersity of 1.3 was used, together with PLA (10 kDa, polydispersity 1.1), to synthesize block copolymers. The prepared nanoparticles had a mean particle size of about 140 nm with a zeta potential of about −20 mV.

The results obtained by the TEM and AFM examinations show that the morphology of the prepared nanoparticles is spherical in shape with a smooth surface. In the stability study, no aggregation or precipitation of nanoparticles was observed during storage for up to 1 month, as a result of the electrostatic repulsion between the negatively charged nanoparticles. With increasing the galactosamine content conjugated on the rhodamine-123-containing nanoparticles, the intensity of fluorescence observed in HepG2 cells increased significantly. Additionally, the intensity of fluorescence observed in HepG2 cells incubated with the nanoparticles with or without galactosamine conjugated increased approximately linearly with increasing the duration of incubation. In contrast, there was no fluorescence observed in Hs68 cells (without ASGP receptors) incubated with the nanoparticles with galactosamine conjugated. The aforementioned results indicated that the galactosylated nanoparticles prepared in the study had a specific interaction with HepG2 cells via ligand-receptor recognition.

Some aspects of the invention relate to a method of treating liver cancers in a patient comprising administering a therapeutically effective amount of nanoparticles composed of γ-PGA-PLA block copolymers conjugated with galactosamine. In one embodiment, the nanoparticles comprise a hydrophobic inner core and a hydrophilic outer shell. In another embodiment, the nanoparticles comprise a hydrophilic inner core and a hydrophobic outer shell. In still another embodiment, the nanoparticles comprise at least one bioactive agent, such as paclitaxel or other cancer drugs.

In a further embodiment, the effective amount of nanoparticles is a particle concentration of up to 100 μg/ml. In some embodiment, the γ-PGA component prior to polymerization has a molecular weight of about 4 kDa with a polydispersity of about 1.3.

In some embodiment, the mean particle size for nanoparticles is in the range of about 10 to 400 nm, preferably in the range of about 100 to 200 nm, and more preferably in the range of about 100 to 150 nm.

Some aspects of the invention relate to a method of treating liver cancers in a patient comprising administering a therapeutically effective amount of nanoparticles composed of γ-PGA-PLA block copolymers conjugated with galactosamine, wherein the nanoparticles are loaded with at least a pharmaceutically active compound or an anticancer drug. In a further embodiment, the pharmaceutically active compound is selected from the group consisting of doxorubicin, adriamycin, cisplatin, taxol, 5-fluorouracil, and combination thereof. In a further embodiment, the pharmaceutically active compound is selected from the group consisting of epipodophyllotoxins, camptothecins, endiyne antibiotics, taxanes, coformycins, anthracycline glycosides, mytomycin, combretastatin, anthrapyrazoles, polyamine biosynthesis inhibitors, and combination thereof.

Some aspects of the invention relate to a compound for treating liver cancers in a patient comprising a therapeutically effective amount of nanoparticles composed of γ-PGA-PLA block copolymers conjugated with galactosamine.

It is one object of the present invention to provide paclitaxel-loaded formulations using a novel type of self-assembled nanoparticles (NPs). In one embodiment, the NPs are composed of block copolymers synthesized by poly(γ-glutamic acid) and poly(lactide). In a further embodiment for the potential of targeting liver cancer cells, galactosamine is conjugated on the prepared nanoparticles (Gal-NPs). In the in vitro studies, it was found that both the NPs and the Gal-NPs have a similar release profile of paclitaxel. The activity in inhibiting the growth of HepG2 cells by the Gal-NPs was comparable to that of a clinically available paclitaxel formulation (Phyxol®), while the NPs of the present invention display a significantly less toxicity. The biodistribution and anti-tumor efficacy of the NPs and the Gal-NPs were studied in hepatoma-tumor-bearing nude mice. It was found that the groups injected with Phyxol®, the NPs or the Gal-NPs significantly delayed the tumor growth as compared to the control group injected with PBS.

Among all study groups, the group injected with the Gal-NPs appeared to have the most significant efficacy in the reduction of the size of the tumor. This is because a large number of the Gal-NPs accumulates at the tumor site, and subsequently releases their encapsulated paclitaxel to inhibit the growth of the tumor. The aforementioned experimental results indicate that the galactosylated nanoparticles prepared in the study have a specific interaction with the hepatoma tumor induced in nude mice via ligand-receptor recognition. Therefore, it is one object of the invention to provide the prepared Gal-NPs as a potential drug delivery system for the targeted delivery to liver cancers. It is another object of the present invention to provide a ligand (such as an antibody) for treating a target tumor or cancer with certain tumor-specific or cancer-specific ligand-receptor recognition.

It is another object of the invention to provide nanoparticles (the NPs) with varying feed weight ratios of paclitaxel to block copolymer (the P/C ratio). In one embodiment, the morphology of all the prepared nanoparticles is spherical in shape with a smooth surface. With increasing the P/C ratio, the drug loading content of the prepared nanoparticles increases significantly, while their drug loading efficiency decreases remarkably. The release rate of paclitaxel from the NPs decreases significantly with increasing the P/C ratio. Cells treated with distinct paclitaxel formulations result in arrest in the G2/M phase. The arrest of cells in the G2/M phase is highly suggestive of interferences by paclitaxel with spindle formation, and is consistent with our morphological findings. In one embodiment, the active targeting nature of the Gal-NPs prepared in the study is used as a potential drug delivery system for the targeted delivery to liver cancers.

The effects of the feeding ratio of drug to copolymer on the particle size, zeta potential, drug loading content and loading efficiency, and release profile of the prepared nanoparticles and their cytotoxicity on HepG2 cells (a liver cancer cell line) from in vitro evaluation are disclosed herein. Additionally, biodistributions of the prepared nanoparticles were studied in vivo in normal mice and hepatoma-tumor-bearing nude mice. The anti-tumor efficacy of the prepared nanoparticles in hepatoma-tumor-bearing nude mice was also examined. The morphology of the prepared nanoparticles was examined by the transmission electron microscopy (TEM) and the atomic force microscopy (AFM). Additionally, the cytotoxicity of the prepared nanoparticles with or without galactosamine conjugated on HepG2 cells (a liver cancer cell line) as compared to that of a clinically available paclitaxel formulation was estimated in vitro. The effect of the prepared nanoparticles to alter cellular microtubules and restrict HepG2 cells in specific cell cycle stages was investigated using a confocal laser scanning microscope (CLSM) and a flow cytometer.

BRIEF DESCRIPTION OF THE DRAWINGS

Additional objects and features of the present invention will become more apparent and the disclosure itself will be best understood from the following Detailed Description of the Exemplary Embodiments, when read with reference to the accompanying drawings.

DETAILED DESCRIPTION OF THE EXEMPLARY EMBODIMENTS

Figure 1:
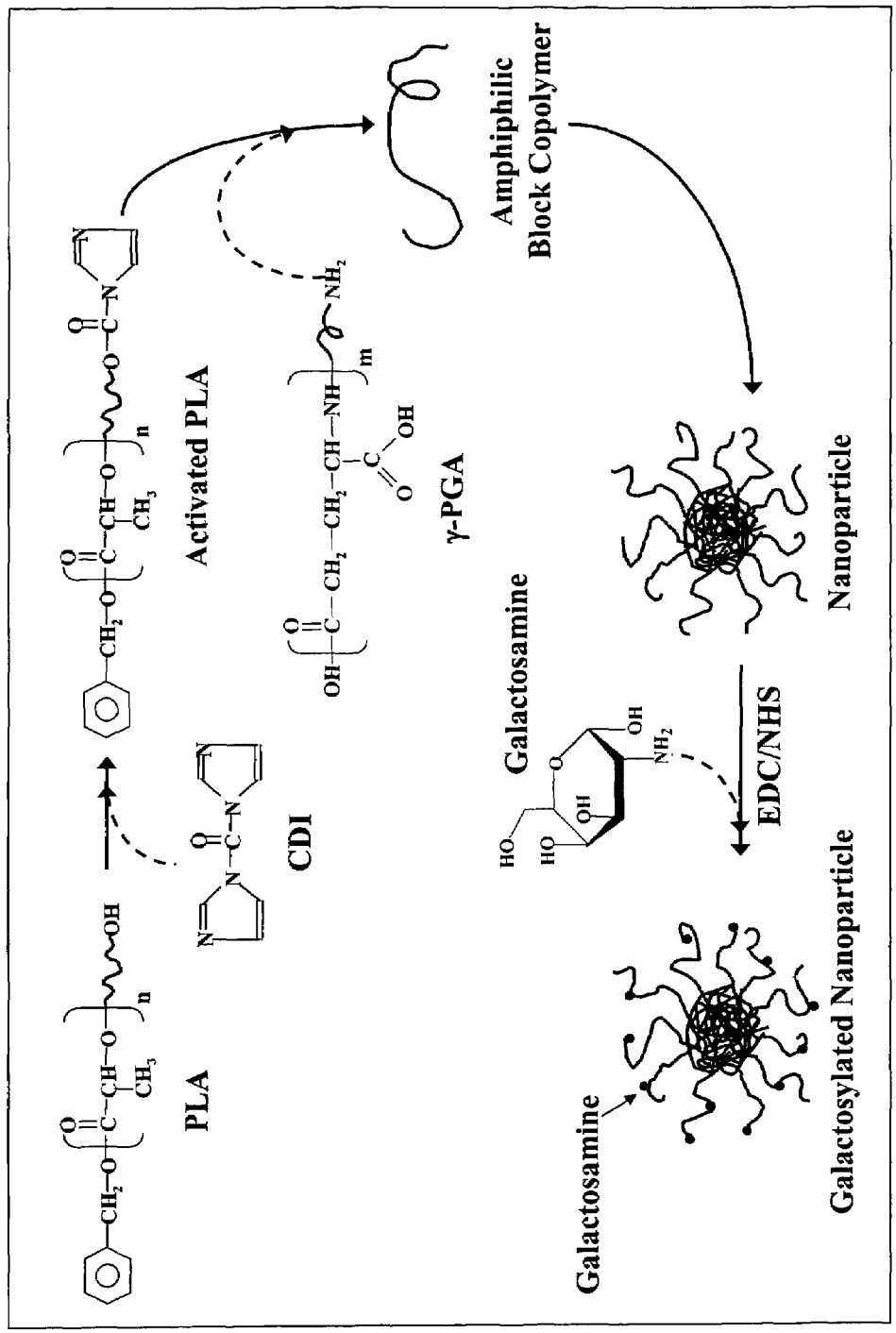
FIG. 1 shows schematic illustrations of synthesis of γ-PGA-PLA block copolymers and formation of self-assembled nanoparticles with galactosamine conjugated.

The preferred embodiments of the present invention described below relate particularly to a preparation of nanoparticles composed of poly(γ-glutamic acid)-poly(lactide) block copolymers that further comprise galactosamine and bioactive agents. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

Over the past few decades, biodegradable nanoparticles composed of amphiphilic block copolymers have attracted considerable interests as an effective drug carrier. Additionally, numerous attempts have been made to increase the effectiveness of anticancer drugs by increasing their concentration at the target site. In this study, biodegradable and biocompatible polymers, γ-PGA and PLA, were used to synthesize γ-PGA-PLA block copolymers via a simple coupling reaction between γ-PGA and PLA to prepare self-assembled nanoparticles. In addition, galactosamine was conjugated on the prepared nanoparticles as a targeting moiety.

γ-PGA is a naturally occurring anionic homo-polyamide that is made of L-glutamic acid units connected by amide linkages between α-amino and γ-carboxylic acid groups (Crit. Rev. Biotechnol. 2001; 21:219-232). It is an exocellular polymer of certain *Bacillus* species that is produced within cells via the TCA cycle and is freely excreted into the fermentation broth. Its exact biological role is not fully known, although it is likely that γ-PGA is linked to increasing the survival of producing strains when exposed to environmental stresses. Because of its water-solubility, biodegradability, edibility, and non-toxicity toward humans and the environment, several applications of γ-PGA in food, cosmetics, medicine, and water treatment have been investigated in the past few years.

Example No. 1

Materials and Methods of Nanoparticles Preparation

PLA is herein an abbreviated term representing poly(L-lactide), Mn at 10 kDa, with a polydispersity of 1.1 determined by the GPC analysis. Dimethyl sulfoxide (DMSO<0.01% water), N,N'-carbonyldiimidazole (CDI, 98%), and dichloromethane were obtained from Fluka (Buchs, Switzerland). L-glutamic acid (>99%), N-(3-dimethylaminopropyl)-N'-ethylcarbodiimide (EDC), N-hydroxysuccinimide (NHS), galactosamine, hydrophobic dye rhodamine-123, and sodium cholate were purchased from Sigma, USA. Pyrene as a fluorescence probe was acquired from Aldrich, USA. 4-Dimethylaminopyridine (DMAP) and 1,4-dioxane was purchased from ACROS (Janssen Pharmaceuticalaan, Belgium). All other chemicals used were reagent grade.

Example No. 2

Production and Purification of γ-PGA

γ-PGA (FIG. 1) was produced by *Bacillus licheniformis* (ATCC 9945, Bioresources Collection and Research Center, Hsinchu, Taiwan) as per the method reported by Yoon et al. with slight modifications (Biotechnol. Lett. 2000; 22:585-588). Highly mucoid colonies (ATCC 9945a) were selected from *Bacillus licheniformis* (ATCC 9945) cultured on the E medium (L-glutamic acid, 20.0 g/l; citric acid, 12.0 g/l; glycerol, 80.0 g/l; NH$_4$Cl, 7.0 g/l; K$_2$HPO$_4$, 0.5 μl; MgSO$_4$.7H$_2$O, 0.5 g/l, FeCl$_3$-6H$_2$O, 0.04 g/l; CaCl$_2$.2H$_2$O, 0.15 g/l; MnSO$_4$.H$_2$O, 0.104 g/l, pH 6.5) agar plates at 37° C. for several times. Subsequently, young mucoid colonies were transferred into 10 ml E medium and grown at 37° C. in a shaking incubator at 250 rpm for 24 hours. Afterward, 500 μl of culture broth was mixed with 50 ml E medium and was transferred into a 2.5-1 jar-fermentor (KMJ-2B, Mituwa Co., Osaka, Japan) containing 950 ml of E medium. Cells were cultured at 37° C. The pH was controlled at 6.5 by automatic feeding of 25% (v/v) NH$_4$OH and 2M HCl. The dissolved oxygen concentration (DOC) was initially controlled at 40% of air saturation by supplying air and by controlling the agitation speed up to 1000 rpm.

After 40 hours, cells were separated from the culture broth by centrifugation for 20 minutes at 12,000×g at 4° C. The supernatant containing γ-PGA was poured into 4 volumes of methanol and left overnight with gentile stirring. The resulting precipitate containing crude γ-PGA was collected by centrifugation for 40 minutes at 12,000×g at 4° C. and then was dissolved in distilled water to remove insoluble impurities by centrifugation for 20 minutes at 24,000×g at 4° C. The aqueous γ-PGA solution was desalted by dialysis (MWCO: 12,000-14,000, Spectrum Laboratories, Inc., Laguna Hills, Calif.) against distilled water for 12 hours with water exchanges several times, and finally was lyophilized to obtain pure γ-PGA.

The purified γ-PGA was confirmed by the proton nuclear magnetic resonance ($^1$H-NMR) and the Fourier transformed infrared (FT-IR) analyses. Analysis of $^1$H-NMR was conducted on a NMR spectrometer (Varian Unityionva 500 NMR Spectrometer, MO) using DMSO-$d_6$ at 2.49 ppm as an internal reference. Test samples used for the FT-IR analysis first were dried and ground into a powder form. The powder then was mixed with KBr (1:100) and pressed into a disk. Analysis was performed on an FT-IR spectrometer (Perkin Elmer Spectrum RX1 FT-IR System, Buckinghamshire, England). The samples were scanned in the range of 400-4,000 cm$^{-1}$.

Figure 2:
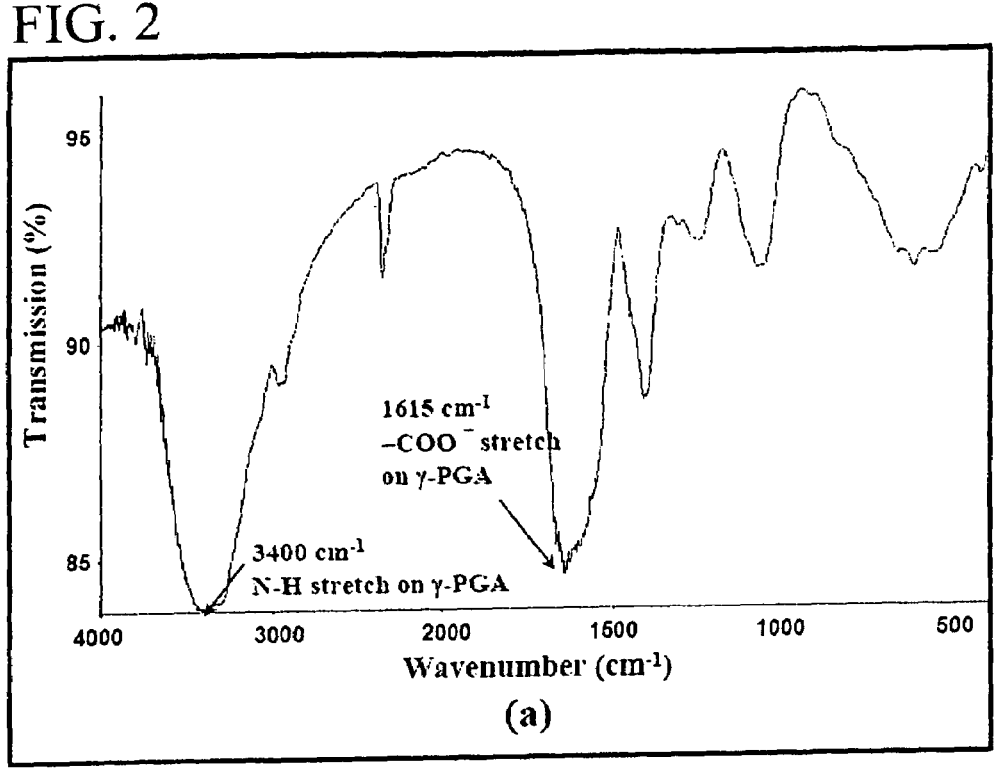
FIG. 2 shows (a) FT-IR and (b) $^1$H-NMR spectra of the purified γ-PGA obtained by microbial fermentation.
Figure 2:
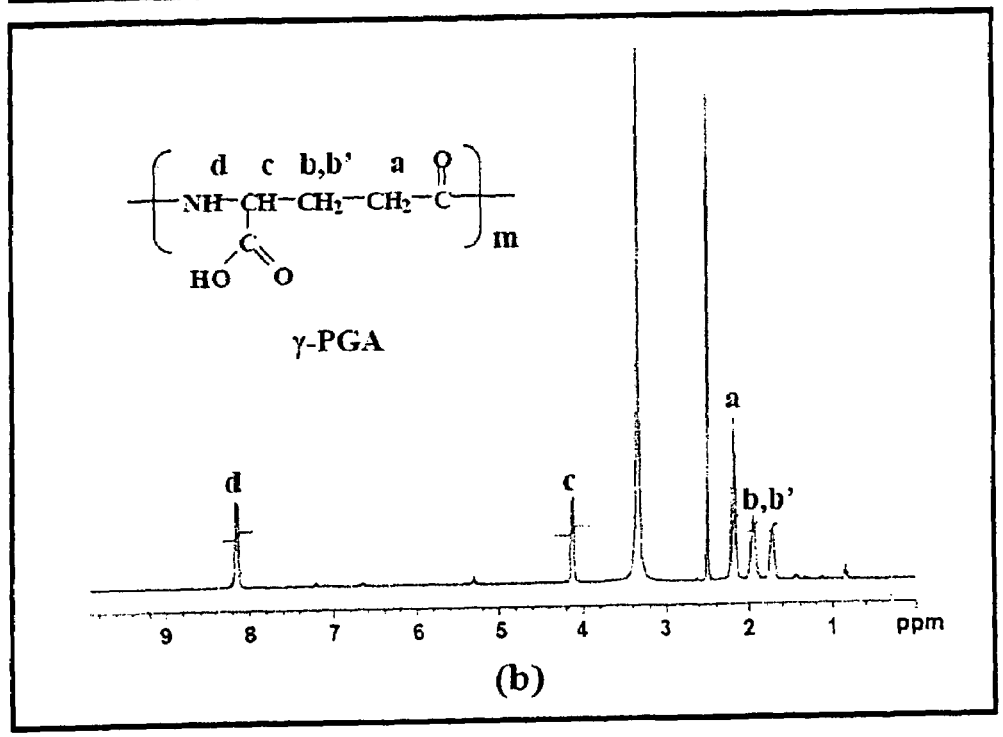

FIG. 2a and FIG. 2b show the FT-IR and $^1$H-NMR spectra of the purified γ-PGA obtained from fermentation, respectively. As shown in the FT-IR spectrum (FIG. 2a), a characteristic band at 1615 cm$^{-1}$ for the associated carboxylic acid salt (—COO$^-$ antisymmetric stretch) on γ-PGA was observed. The characteristic absorption due to the C=O in secondary amides (amide I band) was overlapped by the characteristic band of —COO$^-$. Additionally, the characteristic peak observed at 3400 cm$^{-1}$ was the N—H stretch of γ-PGA. In the $^1$H-NMR spectrum, five chief signals observed at 1.73, 1.94, 2.19, 4.14, and 8.15 ppm represent the protons of β-CH$_2$, γ-CH$_2$, α-CH, and amide, respectively. These results indicated that the observed FT-IR and $^1$H-NMR spectra correspond well to those expected for γ-PGA. Additionally, the fermented product after purification showed no detected macromolecular impurities by the $^1$H-NMR analysis, suggesting that the obtained white power of γ-PGA is highly pure. It was reported that *Bacillus licheniformis* 9945a does not produce extracellular polysaccharide products (Int. J. Biol. Macromol. 1994; 16:265-275).

Example No. 3

Hydrolysis and Analysis of γ-PGA

The average molecular weight (Mn) of the purified γ-PGA obtained via the previous procedure in Example No. 2 was about 320 kDa. The purified γ-PGA was then hydrolyzed in a tightly sealed steel container at 150° C. for distinct durations (J. Biol. Chem. 1973; 248:316-324). The average molecular weight along with the polydispersity of the hydrolyzed γ-PGA were determined by a gel permeation chromatography (GPC) system equipped with a series of PL aquagel-OH columns (one Guard 8 μm, 50×7.5 mm and two MIXED 8 μm, 300×7.5 mm, PL Laboratories, UK) and a refractive index (RI) detector (R12000—F, SFD, Torrance, Calif.). Polyethylene glycol (molecular weights of 106-22,000) and polyethylene oxide (molecular weights of 20,000-1,000,000) standards of narrow polydispersity (PL Laboratories, UK) were used to construct a calibration curve. The mobile phase contained 0.01M NaH$_2$PO$_4$ and 0.2M NaNO$_3$ and was brought to a pH of 7.0. The flow rate of mobile phase was 1.0 ml/min, and the columns and the RI detector cell were maintained at 30° C.

Figure 3:
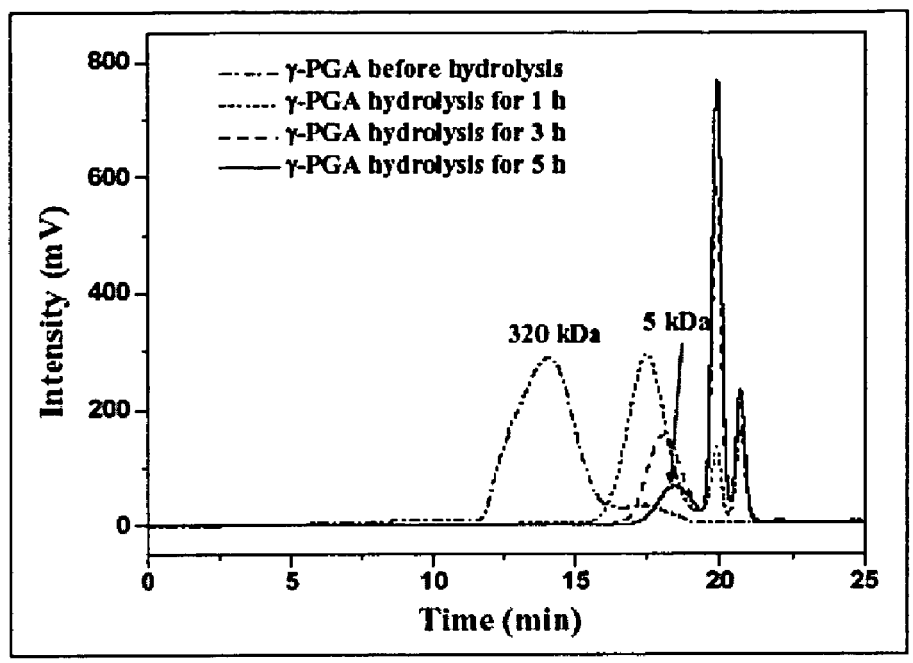
FIG. 3 shows chromatogram of the hydrolyzed γ-PGA obtained in aqueous solution at 150° C. for distinct durations.

In the example, low-molecular-weight γ-PGA was produced by hydrolyzing the purified γ-PGA obtained from fermentation at 150° C. for distinct durations. Hydrolysis of γ-PGA in aqueous solution at different temperatures was proposed as a method to fragment γ-PGA (Biosci. Biotechnol. Biochem. 1992; 56:1031-1035). Solutions of the purified γ-PGA obtained from fermentation and the hydrolyzed γ-PGA were analyzed by a GPC system. As shown in FIG. 3, the purified γ-PGA obtained from fermentation had a high molecular weight (Mn~320 kDa) with a polydispersity of about 1.8. In the hydrolysis of the purified γ-PGA, it was found that the longer duration the hydrolysis, the lower molecular weight of γ-PGA was produced. When γ-PGA was hydrolyzed at 150° C. for 5 hours, the molecular weight of γ-PGA was reduced to about 5 kDa.

It was reported that hydrolysis is not a suitable method to obtain cleaved polymers with a low polydispersity (Bioresource Technol. 2001; 79:207-225). The hydrolyzed γ-PGA with a high polydispersity may affect the coupling efficiency between γ-PGA and PLA and the size distribution of the prepared nanoparticles or micelles. To reduce the polydispersity of the hydrolyzed γ-PGA, the hydrolyzed γ-PGA (~5 kDa) was further dialyzed twice (using a membrane with MWCO: 3500 and a membrane with MWCO: 6000-8000) against distilled water. Thus, obtained γ-PGA had a molecular weight of about 4 kDa with a polydispersity of about 1.3. This specific γ-PGA was used subsequently, together with PLA, to synthesize block copolymers to prepare the nanoparticles.

Example No. 4

Synthesis of γ-PGA-PLA block copolymers

Block copolymers composed of γ-PGA and PLA were synthesized using CDI to activate the terminal hydroxyl groups of PLA (Polymer 1997; 38:6235-6242). CDI (82 mg) was dissolved in 1,4-dioxane (20 ml) in a nitrogen atmosphere and PLA (0.1 g) was subsequently added into the solution. The clear solution was stirred at 37° C. for 2 hours. Afterward, the solution was dialyzed extensively against distilled water at 4° C. Finally, the activated PLA was obtained via centrifugation.

The acidified form of the hydrolyzed γ-PGA (10 mg, Mn=4,000, PDI=1.3) was dissolved in DMSO (5 ml) in a dry, stoppered 20 ml round bottom flask in a nitrogen atmosphere. After dissolution of DMAP (3 mg), a calculated amount of activated PLA (25 mg) was added. The solution was stirred at room temperature for 3 days, after which the reaction was stopped by adding 0.1 ml of concentrated HCl to neutralize DMAP and imidazole. The reaction mixture was transferred to a dialysis tube and dialyzed for 2 days against distilled water for several times at 4° C. Finally, the product (γ-PGA-PLA block copolymers) was lyophilized and stored at −20° C. until used.

Figure 4:
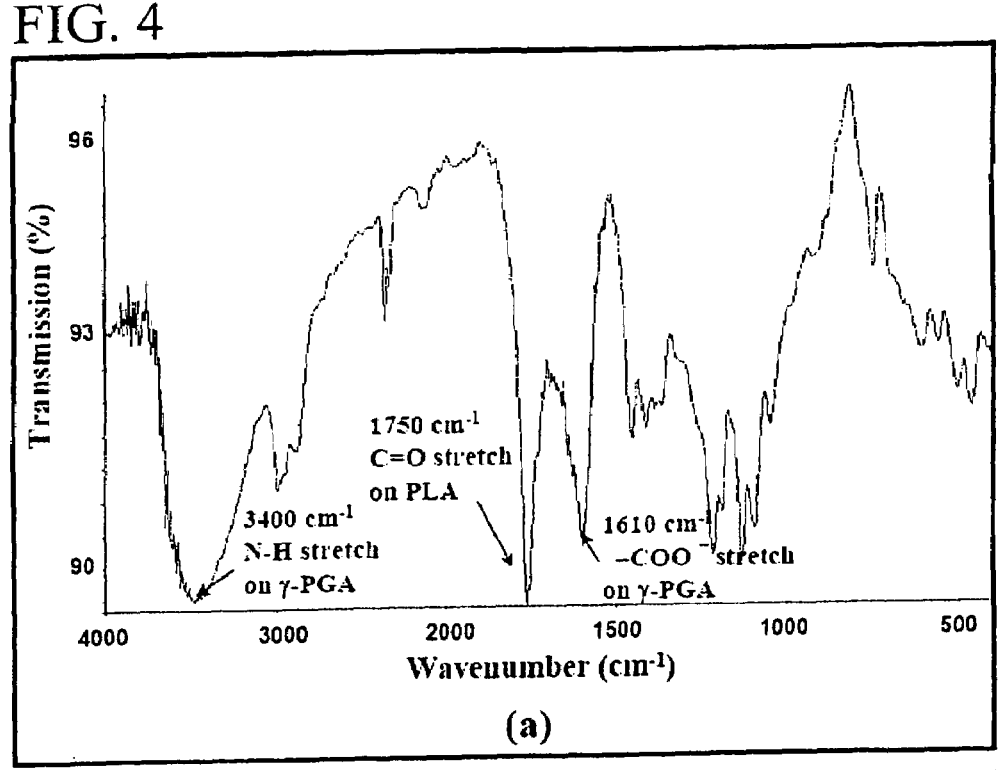
FIG. 4 shows (a) FT-IR and (b) $^1$H-NMR spectra of the synthesized γ-PGA-PLA block copolymer.
Figure 4:
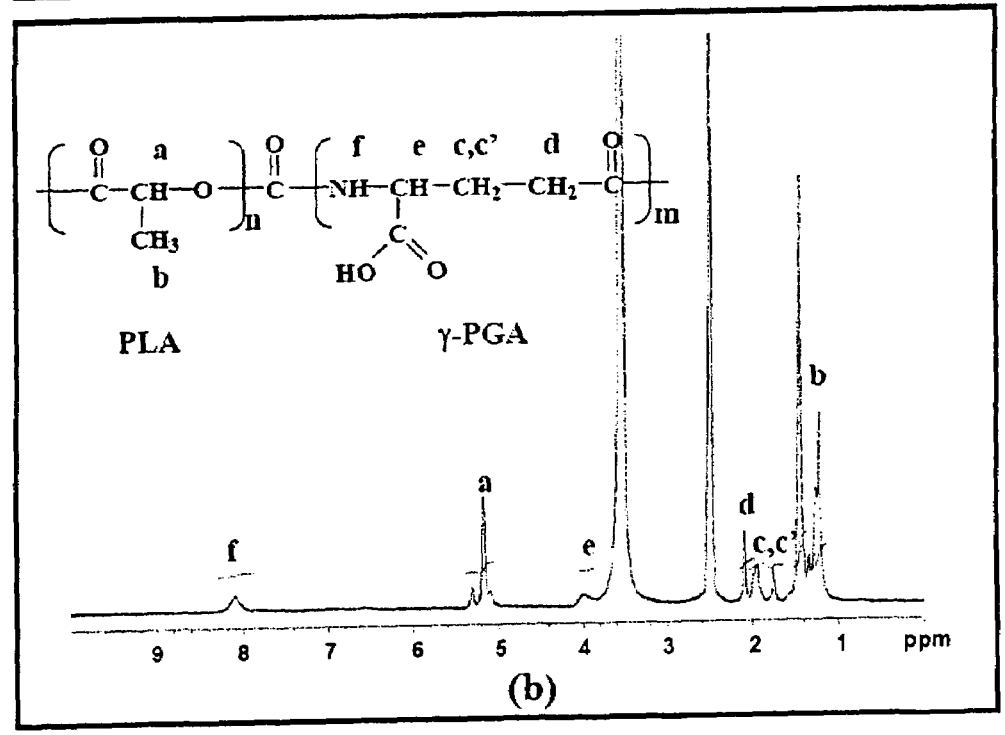

In the experiment, CDI was used to activate the terminal hydroxyl group on PLA, which was then attached to the terminal amine group on γ-PGA to form amphiphilic block copolymers (FIG. 1). CDI has been commonly employed to activate the terminal hydroxyl group on PLA to produce an active derivative that may be attacked by nucleophiles (Anal. Biochem. 1983; 131:25-33). FIG. 4a and FIG. 4b show the FT-IR and $^1$H-NMR spectra of the synthesized γ-PGA-PLA block copolymers, respectively. In the FT-IR spectrum (FIG. 4a), the characteristic peak observed at 1750 cm$^{-1}$ was the C=O stretch on PLA and the characteristic peaks shown at 1610 and 3400 cm$^{-1}$ were the associated carboxylic acid salt (—COO$^-$ antisymmetric stretch) and the N—H stretch on γ-PGA, respectively. In the $^1$H-NMR spectrum (FIG. 4b), the chemical shifts at 1.42 and 5.20 ppm were the protons of methyl group (—CH$_3$) and methine (—CH) on PLA, respectively, while the main chemical shifts on γ-PGA described above were detected as well. The aforementioned results indicated that γ-PGA was successfully conjugated to PLA by CDI.

Example No. 5

Nanoparticle Preparation and Characterization

Nanoparticles were produced using the emulsion/solvent evaporation technique (Colloid. Surface. B, 2000; 18:301-313). Briefly, 10 mg of block copolymers were dissolved in 1 ml methylene chloride, then vortexed and emulsified in 10 ml of a 0.1 wt % sodium cholate solution using a sonicator (VCX-750, Sonics & Materials Inc., Newtown, Conn.) at cycles of 1 second sonication followed by 1 second of pauses, and total time 5 minutes. Afterward, the solvent was evaporated in a vacuum oven at 37° C. for 1 hour. The nanoparticles were then recovered by centrifugation for 20 minutes at 20,000×g at 4° C. Subsequently, the nanoparticles were resuspended by phosphate buffered saline (PBS, pH 7.4, Sigma). The size distribution and zeta potential of nanoparticles were measured using a Zetasizer (3000HS, Malvern Instruments Ltd., Worcestershire, UK).

The transmission electron microscopy (TEM) and atomic force microscopy (AFM) were used to observe the morphology of nanoparticles. The TEM sample was prepared by placing a drop of the nanoparticle solution onto a 400 mesh copper grid coated with carbon. About 2 minutes after deposition, the grid was tapped with a filter paper to remove surface water and negatively stained by using a 2% (by w/v) phosphortungsten acid (PTA) solution. The AFM sample was prepared by casting a drop of the nanoparticle solution on a slide glass and then dried in vacuum.

During storage, aggregation of nanoparticles may occur and thus leads to lose their structural integrity or form precipitation of nanoparticles (Eur. J. Pharm. Sci. 1999; 8:99-107). Therefore, the stability of nanoparticles during storage must be evaluated. In the stability study, the prepared nanoparticles were suspended in PBS (1 mg/ml) at 4° C. and their particle size and zeta potential during storage were monitored by a Zetasizer.

Figure 5:
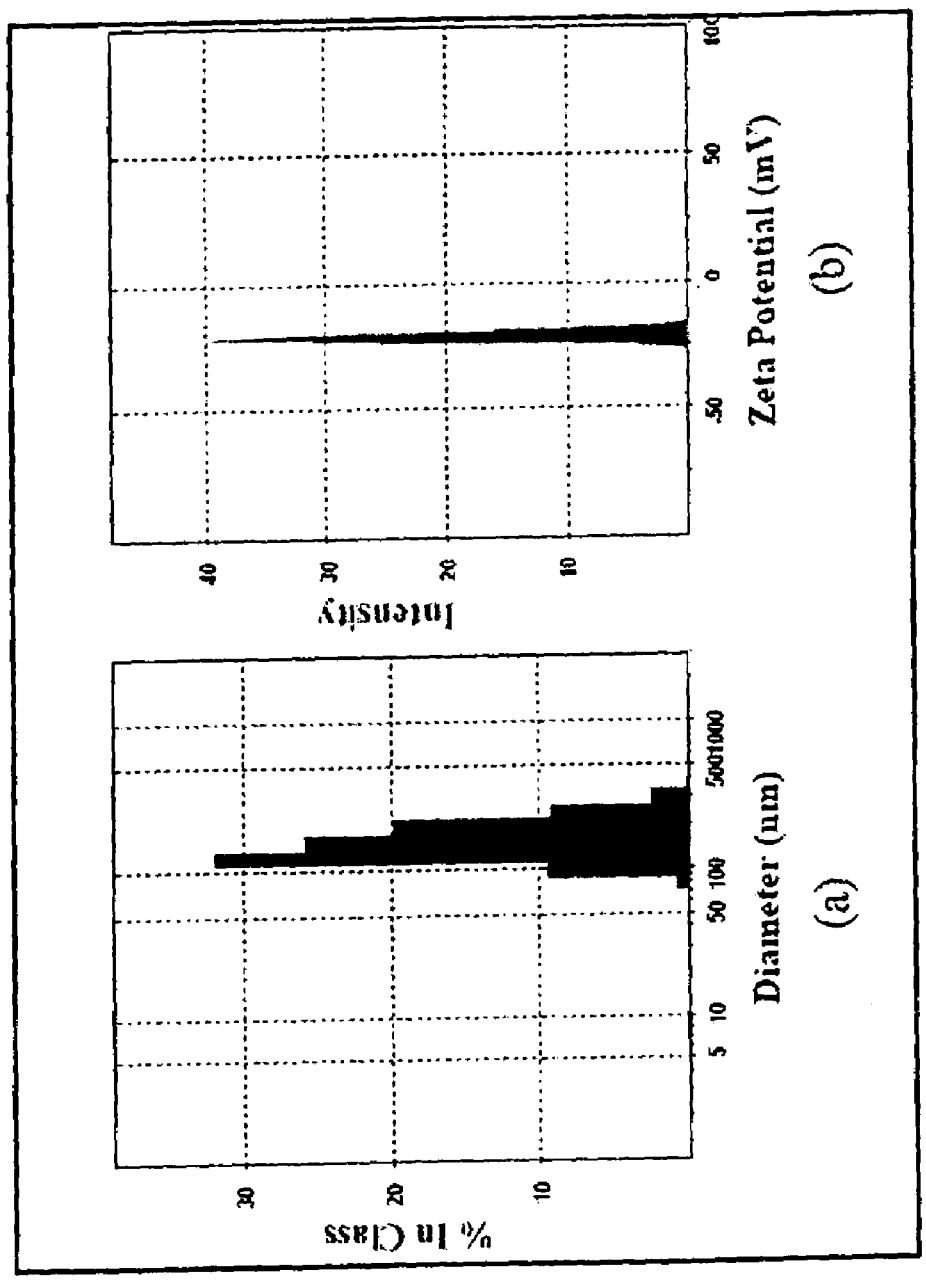
FIG. 5 shows (a) size distribution and (b) zeta potential of the prepared nanoparticles composed of γ-PGA-PLA block copolymers without galactosamine conjugated.

The size distribution and zeta potential of the nanoparticles without galactosamine conjugated in aqueous solution were investigated by dynamic light scattering. Size distribution and zeta potential may play important roles in determining the fate of nanoparticles after administration (Biomaterials 2004; 25:2843-2849). FIG. 5a and FIG. 5b show representative particle size and zeta potential distributions of the prepared nanoparticles. As shown, the prepared nanoparticles had a mean particle size of about 140 nm (FIG. 5a). Some aspects of the present invention provide a compound for treating liver cancers in a patient comprising a therapeutically effective amount of nanoparticles composed of γ-PGA-PLA block copolymers conjugated with galactosamine, wherein the mean particle size for nanoparticles is in the range of about 50 to 400 nm, preferably in the range of about 100 to 200 nm, and more preferably in the range of about 100 to 150 nm. Hashida et al. reported that the majority of the fenestrate of the liver sinusoid is usually smaller than 200 nm in diameter (J. Control. Release 1998; 53:301-310). Thus, large particles hardly reach the liver's parenchymal cells. Additionally, drug carriers with a diameter larger than 200 nm are readily scavenged non-specifically by monocytes and the reticuloendothelial system (Biochim. Biophys. Acta, 1994; 1190:99-107). It was reported that smaller particles tended to accumulate in the tumor sites due to the EPR (enhanced permeability and retention) effect (Crit. Rev. Ther. Drug Carrier Syst. 1989; 6:193-210) and a greater internalization was also observed (Adv. Drug Deliver. Rev. 2002; 54:695-713).

It was found that the prepared nanoparticles had a negative surface charge with a zeta potential of about −20 mV (FIG. 5b) due to the carboxyl (—COO$^-$) groups on the hydrophilic γ-PGA shell. This may affect the cellular uptake of the prepared nanoparticles due to electrostatic repulsion forces between the nanoparticles and the rather negatively charged surface of cells (Adv. Drug Deliver. Rev. 2002; 54:695-713). However, Li et al. reported that their conjugated paclitaxel onto α-PGA does not diminish the EPR effect and the accumulation and retention of α-PGA-paclitaxel in solid tumors (Adv. Drug Deliver. Rev. 2002; 54:695-713).

They suggested that specific receptor-mediated interactions of α-PGA-drug conjugates containing targeting ligands might also increase the rate of polymer uptake into the target cells. Additionally, Hashida et al. suggested that the negatively charged carriers may be suitable for the selective delivery of drugs or pDNA to the liver's parenchymal cells, since the cationic nature of macromolecules and macromolecular drug conjugates may lead to non-specific binding to various cells after systemic administration (J. Control. Release 1998; 53:301-310).

Figure 6:
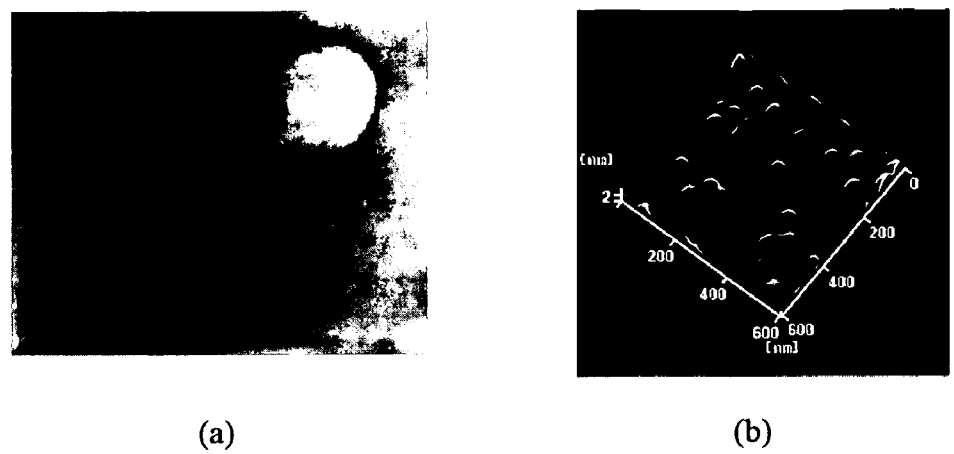
FIG. 6 shows morphology of the prepared nanoparticles composed of γ-PGA-PLA block copolymers: (a) TEM micrograph and (b) AFM micrograph.

The results obtained by the TEM and AFM examinations showed that the morphology of the prepared nanoparticles was spherical in shape with a smooth surface (FIG. 6). The diameters of nanoparticles observed by TEM and AFM were generally smaller than that obtained by dynamic light scattering. This is because the diameter of nanoparticles obtained by dynamic light scattering reflected the hydrodynamic diameter of nanoparticles swelled in aqueous solution, while those observed by TEM and AFM were the diameters of dried nanoparticles.

Figure 7:
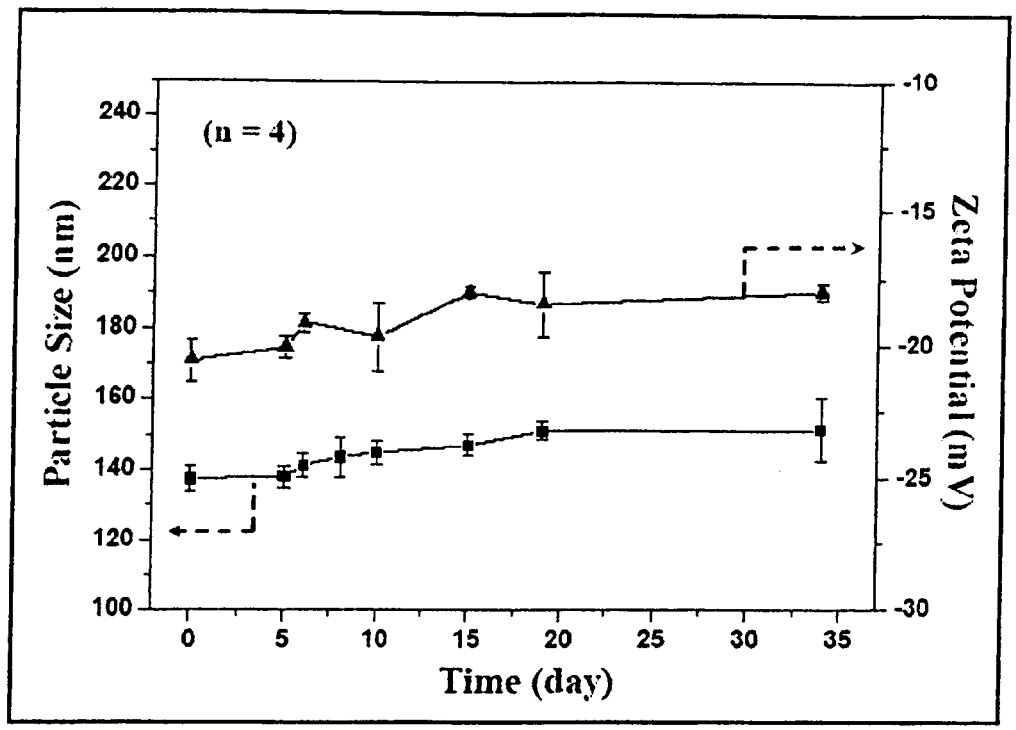
FIG. 7 shows changes in particle size (■, mean diameter) and zeta potential (▲) of the nanoparticles (1 mg/ml in PBS) during storage.

In the stability experiment, no aggregation or precipitation of nanoparticles was observed during storage for up to 1 month, as a result of the electrostatic repulsion between the negatively charged nanoparticles. Additionally, changes in particle size and zeta potential of the nanoparticles throughout the entire course of the study were minimal (FIG. 7). These results demonstrated that the prepared nanoparticles suspended in PBS were rather stable during storage.

Example No. 6

Fluorescence Spectroscopy (Pyrene)

The micellization of block copolymers in aqueous solutions depends on their concentration. Pyrene solubilization was used for the determination of the critical micelle concentration (CMC) in block copolymer solutions (Macromolecules 1995; 28:2303-2314). Stock solutions of pyrene (6.0×10$^{-2}$M) were prepared in acetone and stored at 4° C. until used (J. Control. Release 2003; 90:363-374). For the measurement of steady-state fluorescence spectra, the stock pyrene solution was added to DI water to give a pyrene concentration of 12.0×10$^{-7}$M. Subsequently, the solution was placed in a vacuum oven at 60° C. for 1 hour to remove acetone from the solution. The acetone-free pyrene solution was mixed together with solutions of nanoparticles of which the concentration ranged from $5\times10^{-5}$ to 0.5 mg/ml. The final concentration of pyrene in each sample solution was $6.0\times10^{-7}$M, which is nearly equal to its solubility in water at room temperature. The emission wavelength at 395 nm was recorded on a spectrofluorometer (F-2500, Hitachi, Tokyo, Japan).

Figure 8:
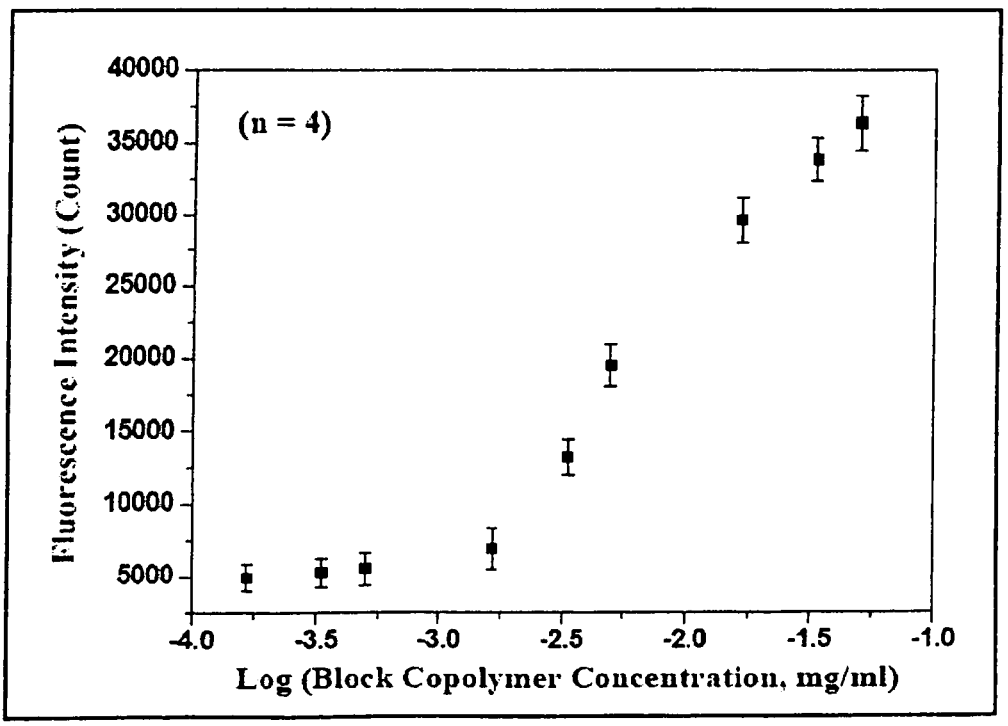
FIG. 8 shows plot of the fluorescence emission intensity of pyrene ($6.0\times10^{-7}$M) versus the γ-PGA-PLA block copolymer concentration ($\lambda_{excitation}$=333 nm, $\lambda_{emission}$=395 nm).

To determine the critical micelle concentration (CMC) of nanoparticles in DI water, florescence measurements were carried out using pyrene as a probe (J. Control. Release 2003; 90:363-374). Pyrene is sensitive to changes in its environment, thus allows estimating the amounts of pyrene in nanoparticles at concentrations exceeding the CMC (Macromolecules 1995; 28:2303-2314). As shown in FIG. 8, the CMC of nanoparticles was about 2.3 µg/ml. The fluorescence intensity measured remained virtually constant below the CMC. Above the CMC, the fluorescence intensity increased substantially, indicating the incorporation of pyrene in the hydrophobic core of nanoparticles.

Example No. 7

Conjugation of Galactosamine to the Surface of Nanoparticles

Galactosamine (0, 2.5, or 10 mg/ml) was conjugated to the surface of nanoparticles (1 mg/ml) via an amide linkage by EDC in the presence of NHS (J. Biomed. Mat. Res. 2003; 64A:427-438; J. Appl. Polym. Sci. 2004; 91:4017-4026). The obtained nanoparticles were separated from unreacted molecules via ultrafiltration and then lyophilized. The amounts of galactosamine conjugated on nanoparticles were determined by the Morgan Elson assay (Bioconj. Chem. 2001; 12:890-899).

Example No. 8

Cell Uptake

In the examples, rhodamine-123 was used as a model hydrophobic fluorescent probe that can be encapsulated in the hydrophobic core in the preparation of nanoparticles with or without the conjugation of galactosamine for confocal laser scanning microscopy studies. Free rhodamine-123 was removed from the rhodamine-123-containing nanoparticle suspension via ultrafiltration. The rhodamine-123-containing nanoparticle suspension was then filtered through a 0.45 µm membrane for sterilization. Subsequently, 100 µl of rhodamine-123-containing nanoparticles (1 mg/ml) were added to HepG2 or human foreskin fibroblast (Hs68) cells, which were pre-cultured on a 35-mm glass dish for 0.24 hours. The experimental temperature was maintained at 37° C. by a temperature control system (DH-35 Culture Dish Heater, Warner Instruments Inc. Hamden, Conn.). After incubation for specific time intervals, the differential interference contrast (DIC) and fluorescence images were obtained real-time by using an inversed confocal laser scanning microscope (TCS SL, Leica, Germany). The fluorescence images were observed using an argon laser (excitation at 488 nm, emission collected at a range of 510-540 nm) and the quantitative analysis was performed using LCS Lite software (version 2.0).

Table 1 shows the mean particle size, zeta potential, and galactosamine content of the prepared nanoparticles with or without galactosamine conjugated. In the table, NPs represents the prepared nanoparticles without galactosamine conjugated. In the preparation of the nanoparticles conjugated with galactosamine, 2.5 or 10 mg/ml of galactosamine was added to 1 mg/ml of nanoparticles in the presence of EDC and NHS, thus obtained particles were termed Gal-NPs-2.5 and Gal-NPs-10, respectively, in the following discussion. It was found that the mean particle sizes of nanoparticles conjugated with galactosamine (Gal-NPs-2.5 and Gal-NPs-10) were similar to that without galactosamine conjugated (NPs, $p>0.05$), while the values of their zeta potential decreased significantly ($p<0.05$). This is because galactosamine was conjugated to the carboxyl ($-COO^-$) groups on γ-PGA and thus reduced the negative surface charge of the prepared nanoparticles (Gal-NPs-2.5 and Gal-NPs-10).

TABLE 1

Mean particle size, zeta potential, and galactosamine content of the prepared nanoparticles with or without galactosamine conjugated.

| Samples (n = 4) | Mean Particle Size (nm) | Zeta Potential (mV) | Galactosamine Content (nmol/mg nanoparticles) |
|---|---|---|---|
| NPs[&] | 140.6 ± 5.5 | −19.3 ± 3.4 | 0 |
| Gal-NPs-2.5* | 138.2 ± 6.7 | −15.4 ± 2.6 | 19.3 ± 2.5 |
| Gal-NPs-10* | 143.5 ± 4.2 | −11.2 ± 3.6 | 65.7 ± 3.6 |

[&]NPs: the prepared nanoparticles without galactosamine conjugated.
*Gal-NPs: the prepared nanoparticles with galactosamine conjugated.

Hepatocytes are known to recognize galactose- and N-acetylgalactosamine-terminated glycoproteins via the asialoglycoprotein (ASGP) receptors located on their surfaces (Int. J. Pharm. 1999; 188:39-47). Once a ligand binds to the ASGP receptor, the ligand-receptor complex is rapidly internalized by hepatocytes and the receptor recycles back to the surface of hepatocytes (Adv. Drug Deliver. Rev. 1989; 4:49-63). It was reported that the ASGP receptors are also abundantly expressed on the surfaces of various hepatoma cell lines (Adv. Drug Deliver. Rev. 1989; 4:49-63). To assess the extents of internalization of the prepared nanoparticles into HepG2 cells, NPs, Gal-NPs-2.5, and Gal-NPs-10 were labeled with rhodamine-123. Human foreskin fibroblast (Hs68) cells, which do not possess ASGP receptors, were used as a control cell line.

Figure 9A:
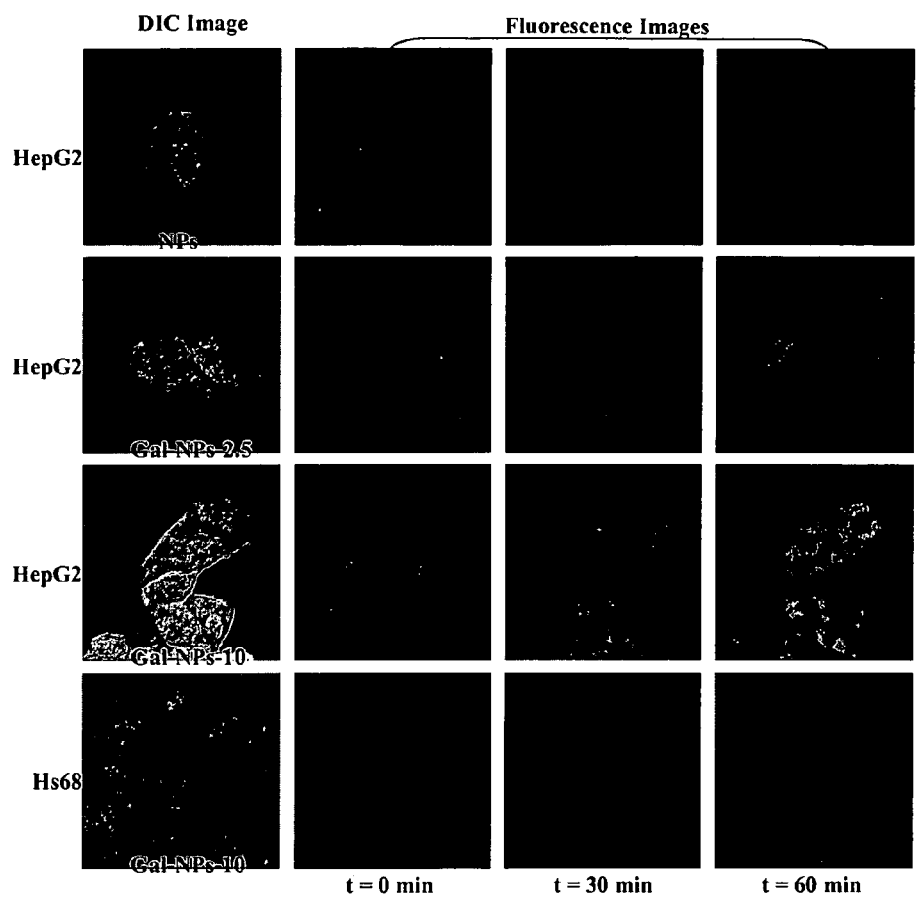
FIG. 9A shows differential interference contrast (DIC) and fluorescence images of HepG2 or Hs68 cells after incubating with the rhodamine-123-containing nanoparticles with or without galactosamine conjugated at 37° C. for distinct durations.
Figure 9B:
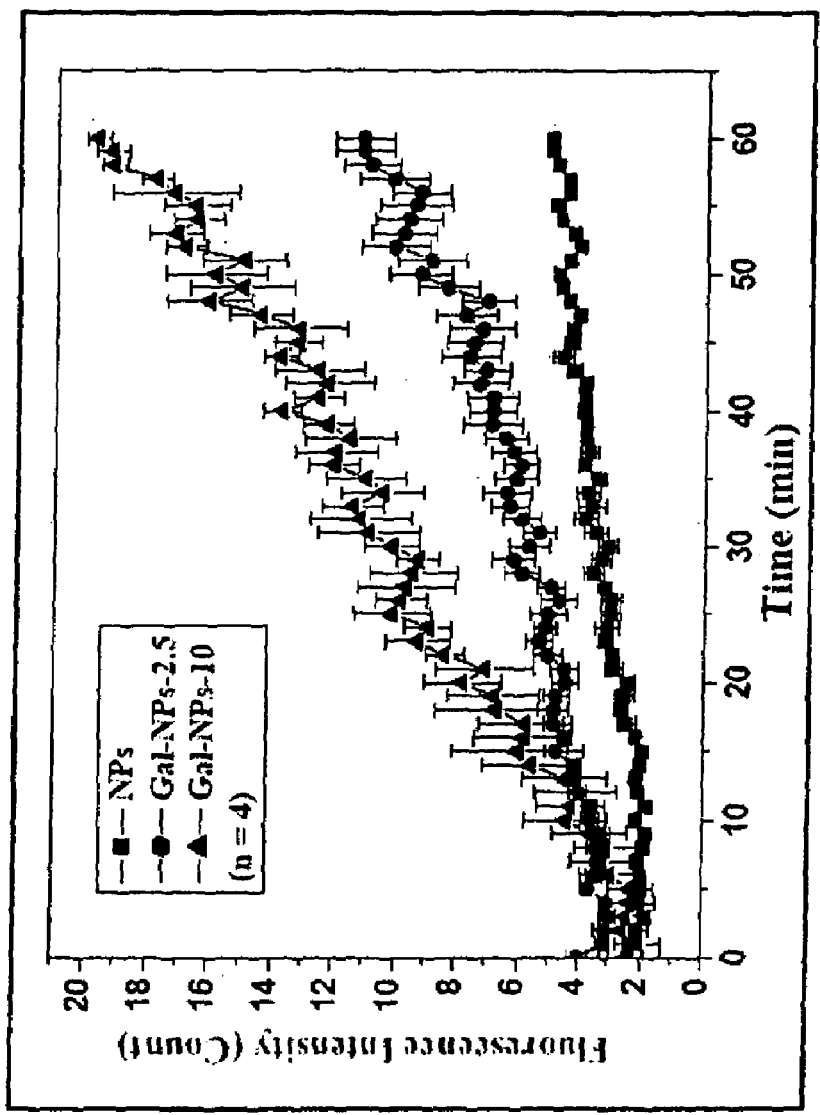
FIG. 9B shows the fluorescence intensity observed in HepG2 cells incubated with the rhodamine-123-containing nanoparticles with or without galactosamine conjugated at 37° C. for distinct durations.

Results of the differential interference contrast (DIC) and fluorescence images of HepG2 or Hs68 cells after incubating with rhodamine-123-containing nanoparticles with or without galactosamine conjugated at 37° C. for distinct durations are shown in FIG. 9A. The intensity of fluorescence observed in cells was analyzed using software (FIG. 9B). FIG. 9B shows the fluorescence intensity observed in HepG2 cells incubated with the rhodamine-123-containing nanoparticles with or without galactosamine conjugated at 37° C. for distinct durations. In FIGS. 9A and 9B, NPs are the prepared nanoparticles without galactosamine conjugated; and Gal-NPs are the prepared nanoparticles with galactosamine conjugated. As shown, in the incubation with NPs, little fluorescence was observed in HepG2 cells on the images taken at 30 and 60 minutes after incubation (FIGS. 9A and 9B). With increasing the galactosamine content conjugated on nanoparticles (Gal-NPs-2.5 and Gal-NPs-10), the intensity of fluorescence observed in HepG2 cells increased significantly ($p<0.05$). Additionally, the intensity of fluorescence observed in HepG2 cells incubated with the nanoparticles with or without galactosamine conjugated (NPs, Gal-NPs-2.5, or Gal-NPs-10) increased approximately linearly with increasing the duration of incubation (FIG. 9B). In contrast, there was no fluorescence observed in Hs68 cells (that is, without ASGP receptors) incubated with the nanoparticles with galactosamine conjugated. The aforementioned results indicated that the galactosylated nanoparticles prepared in the study had a specific interaction with HepG2 cells via ligand-receptor (ASGP) recognition.

Example No. 9

Cytotoxicity of Nanoparticles

Cytotoxicity of the prepared nanoparticles was evaluated in vitro using the MTT assay (J. Biomed Mater. Res. 2002; 61:360-369). The assay is based on mitochondrial dehydrogenase cell activity as an indicator of cell viability. Briefly, MTT [3-(4,5-dimethyl-thiazol-yl)-2,5-diphenyltetrazolium bromide, Sigma, St. Louis, Mo.] was dissolved in PBS with a concentration of 5 mg/ml as a stock MTT solution and filtered for sterilization. HepG2 cells were seeded in 24-well plates at $5 \times 10^4$ cells/well and were allowed to adhere overnight. The growth medium was replaced with a fresh one containing 0-100 μg/ml nanoparticles. The cells were then incubated for 48 hours and washed twice by 1 ml PBS. Subsequently, the cells were incubated in a growth medium containing 1 mg/ml MTT agent for an additional 4 hours at 37° C. and 500 μl of DMSO was added to each well to ensure solubilization of formazan crystals. Finally, the optical density readings were performed using a multiwell scanning spectrophotometer (MRX Microplate Reader, Dynatech Laboratories Inc., Chantilly, Va.) at a wavelength of 570 nm.

The effect of the prepared nanoparticles on cell viability was evaluated by the MTT assay. No significant cytotoxicity to HepG2 cells was observed for a particle concentration of up to 100 μg/ml. This indicated that the effect of cell viability on the cellular uptake of the prepared nanoparticles (with a particle concentration of 50 μg/ml) could be excluded in the studies.

Some aspects of the invention are related to the nanoparticles composed of γ-PGA-PLA block copolymers conjugated with galactosamine as a potential drug delivery system for treating liver cancers.

Example No. 10

Anticancer Drugs

Some aspects of the invention relate to a method of treating liver cancers in a patient comprising administering a therapeutically effective amount of nanoparticles composed of γ-PGA-PLA block copolymers conjugated with galactosamine, wherein the nanoparticles are loaded with at least one anticancer drug. Drugs such as doxorubicin, adriamycin, cisplatin, taxol, and 5-fluorouracil are being widely used in chemotherapies for the treatment of cancer. In the aforementioned Example no. 5, nanoparticles were produced using the emulsion/solvent evaporation technique by mixing effective amounts of raw material (namely γ-PGA, PLA, and at least one selected anticancer drug), followed by conjugation with galactosamine.

Nanoparticle preparations, mainly used for intravenous injection, are employed for targeting hepatoma cells or other solid tumors. When nanoparticle or micelle preparations of anticancer drugs of the present invention are administered, the size of particles ranging from tens to hundreds of nanometers let them penetrate into tumor tissues across the wall of blood vessel that have loosened cell contact and have specific affinity to cancer cells.

U.S. Pat. No. 6,752,981, the entire contents of which are incorporated herein by reference, discloses preferred classes of anticancer drugs including: epipodophyllotoxins, camptothecins, endiyne antibiotics, taxanes, coformycins, anthracycline glycosides, mytomycin, combretastatin, anthrapyrazoles, and polyamine biosynthesis inhibitors.

Preferred epipodophyllotoxins include Etoposide, Teniposide, NK-611, GL-331, and azatoxin. Preferred camptothecins include Camptothecin, Topotecan, Irinotecan (CPT-11), Lurtotecan (GI 147211), 9-aminocamptothecin, GG-211, DX-8951F, SKF 107874, and SKF 108025. Preferred taxanes include paclitaxel, docetaxel, and FCE-28161. Preferred combretastatins include combretastatin A-4 and the reported (S,S) dioxolane analog (Bioorg. Med. Chem. Lett. 88: 1997-2000 (1998). Preferred anthrapyrazoles include mitoxantrone, piroxantrone, and Losoxantrone. Preferred Anthracyclines include Doxorubicin, Daunorubicin, Idarubicin, Pirarubicin, and Epirubicin. Preferred Enediyne Antibiotics include neocarzinostatin, calicheamicin, and esperamicin. In another aspect, Mitomycin is also preferred. Preferred Polyamine Biosynthesis Inhibitors include eflornithine.

Example No. 11

Materials Composition

In this example, Paclitaxel powder (purity>99%) and clinical commercial paclitaxel [Phyxol®, contained 6 mg paclitaxel, 527 mg Cremaphor EL and 47.7% (v/v) alcohol per milliliter] were obtained from Sinphar Pharmaceutical Co., Ltd. (Taipei, Taiwan). PLA [poly(L-lactide), Mn: 10 kDa, with a polydispersity of 1.1 determined by the GPC analysis] was supplied by the Biomedical Engineering Center, Industrial Technology Research Institute (Hsinchu, Taiwan). Dimethyl sulfoxide (DMSO<0.01% water), N,N'-carbonyldiimidazole (CDI, 98%), and dichloromethane were acquired from Fluka (Buchs, Switzerland). L-glutamic acid (purity>99%), N-(3-dimethylaminopropyl)-N'-ethylcarbodiimide (EDC), N-hydroxysuccinimide (NHS), galactosamine, and sodium cholate were purchased from Sigma (St. Louis, Mo.). 4-Dimethylaminopyridine (DMAP) and 1,4-dioxane were obtained from ACROS (Janssen Pharmaceuticalaan, Belgium). All other chemicals used are reagent grade.

Example 12

Production and Purification of γ-PGA

γ-PGA (FIG. 1) was produced by *Bacillus licheniformis* (ATCC 9945, Bioresources Collection and Research Center, Hsinchu, Taiwan) as per the method reported by Yoon et al. with slight modifications (Biotechnol. Lett. 2000; 22:585-588). Highly mucoid colonies (ATCC 9945a) were selected from *Bacillus licheniformis* (ATCC 9945) cultured on the E medium (L-glutamic acid, 20.0 g/l; citric acid, 12.0 g/l; glycerol, 80.0 g/l; $NH_4Cl$, 7.0 g/l; $K_2HPO_4$, 0.5 g/l; $MgSO_4 \cdot 7H_2O$ 0.5 g/l, $FeCl_3 \cdot 6H_2O$, 0.04 g/l; $CaCl_2 \cdot 2H_2O$, 0.15 g/l; $MnSO_4 \cdot H_2O$, 0.104 g/l, pH 6.5) agar plates at 37° C. for several times. Subsequently, young mucoid colonies were transferred into 10 ml E medium and grown at 37° C. in a shaking incubator at 250 rpm for 24 hours. Afterward, 500 μl of culture broth was mixed with 50 ml E medium and was transferred into a 2.5-1 jar-fermentor (KMJ-2B, Mituwa Co., Osaka, Japan) containing 950 ml of E medium. Cells were cultured at 37° C. The pH was controlled at 6.5 by automatic feeding of 25% (v/v) $NH_4OH$ and 2M HCl. The dissolved oxygen concentration (DOC) was initially controlled at 40% of air saturation by supplying air and by controlling the agitation speed up to 1000 rpm.

After 40 hours, cells were separated from the culture broth by centrifugation for 20 minutes at 12000×g at 4° C. The supernatant containing γ-PGA was poured into 4 volumes of methanol and left overnight with gentle stirring. The resulting precipitate containing crude γ-PGA was collected by centrifugation for 40 minutes at 12,000×g at 4° C. and then was dissolved in distilled water to remove insoluble impurities by centrifugation for 20 minutes at 24,000×g at 4° C. The aqueous γ-PGA solution was desalted by dialysis (MWCO: 12,000-14,000, Spectrum Laboratories, Inc., Laguna Hills, Calif.) against distilled water for 12 hours with water exchanges several times, and finally was lyophilized to obtain pure γ-PGA.

The purified γ-PGA was confirmed by the proton nuclear magnetic resonance ($^1$H-NMR) and the Fourier transformed infrared (FT-IR) analyses. Analysis of $^1$H-NMR was conducted on an NMR spectrometer (Varian Unityionva 500 NMR Spectrometer, MO) using DMSO-$d_6$ at 2.49 ppm as an internal reference. Test samples used for the FT-IR analysis first were dried and ground into a powder form. The powder then was mixed with KBr (1:100) and pressed into a disk. Analysis was performed on an FT-IR spectrometer (Perkin Elmer Spectrum RX1 FT-IR System, Buckinghamshire, England). The samples were scanned in the range of 400-4000 cm$^{-1}$.

In the $^1$H-NMR spectrum of the purified γ-PGA obtained from fermentation, five chief signals observed at 1.73, 1.94, 2.19, 4.14, and 8.15 ppm representing the protons of β-$CH_2$, γ-$CH_2$, α-CH, and amide, respectively. Additionally, the fermented product after purification showed no detected macromolecular impurities by the $^1$H-NMR analysis, suggesting that the obtained white power of γ-PGA was highly pure.

Example No. 13

Hydrolysis of γ-PGA

The average molecular weight (Mn) of the purified γ-PGA obtained via the previous fermentation procedure was about 320 kDa. The purified γ-PGA was then hydrolyzed in a tightly sealed steel container at 150° C. for distinct durations (J. Biol. Chem. 1973; 248:316-324). The average molecular weight along with the polydispersity of the hydrolyzed γ-PGA were determined by a gel permeation chromatography (GPC) system equipped with a series of PL aquagel-OH columns (one Guard 8 μm, 50×7.5 mm and two MIXED 8 μm, 300×7.5 mm, PL Laboratories, UK) and a refractive index (RI) detector (RI2000-F, SFD, Torrance, Calif.). Polyethylene glycol (molecular weights of 106-22000 g/mol) and polyethylene oxide (molecular weights of 20,000-1,000,000 g/mol) standards of narrow polydispersity (PL Laboratories, UK) were used to construct a calibration curve. The mobile phase contained $0.01MNaH_2PO_4$ and $0.2MNaNO_3$ and was brought to a pH of 7.0. The flow rate of mobile phase was 1.0 ml/min, and the columns and the RI detector cell were maintained at 30° C.

Figure 10:
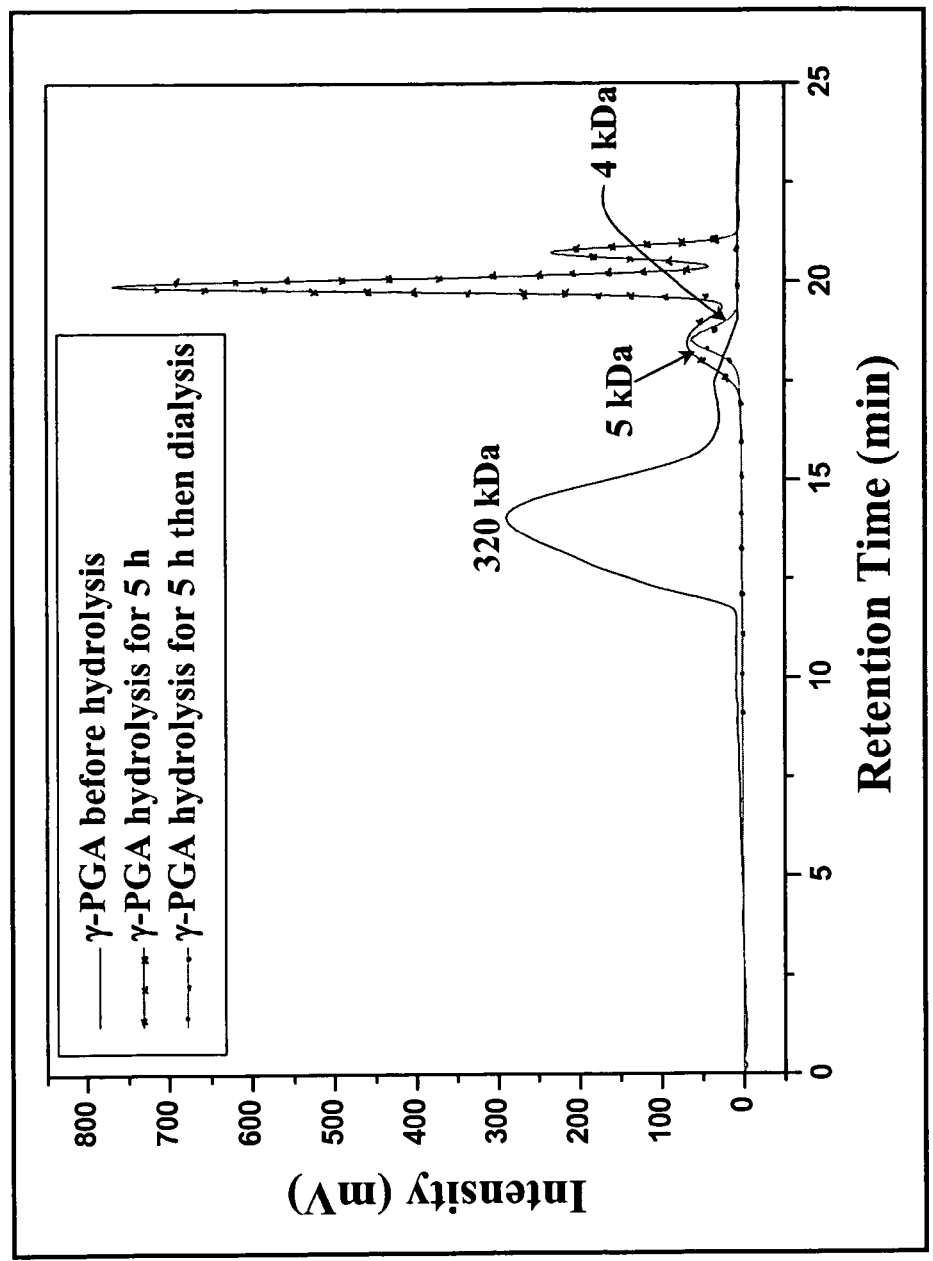
FIG. 10 shows chromatograms of the purified γ-PGA obtained from fermentation (γ-PGA before hydrolysis), the obtained γ-PGA after a 5-h hydrolysis at 150° C. (γ-PGA hydrolysis for 5 h), and the hydrolyzed γ-PGA after dialysis twice against deionized water (γ-PGA hydrolysis for 5 h then dialysis).
Figure 11:
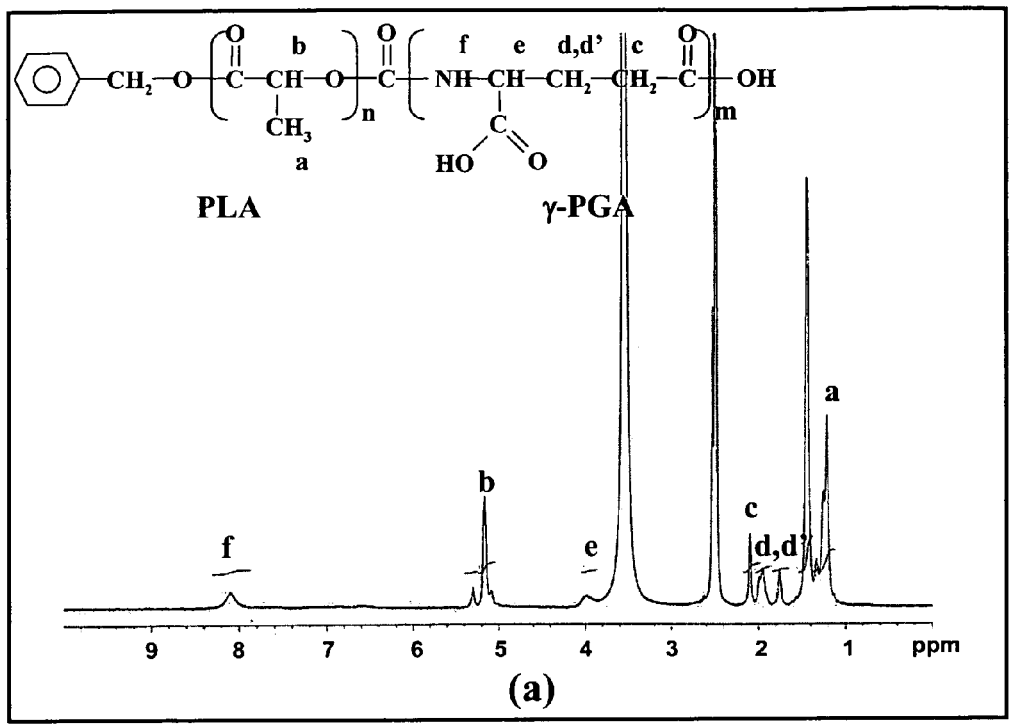
FIG. 11 shows (a) $^1$H-NMR spectrum and (b) GPC chromatogram of the synthesized γ-PGA-PLA block copolymer.
Figure 11:
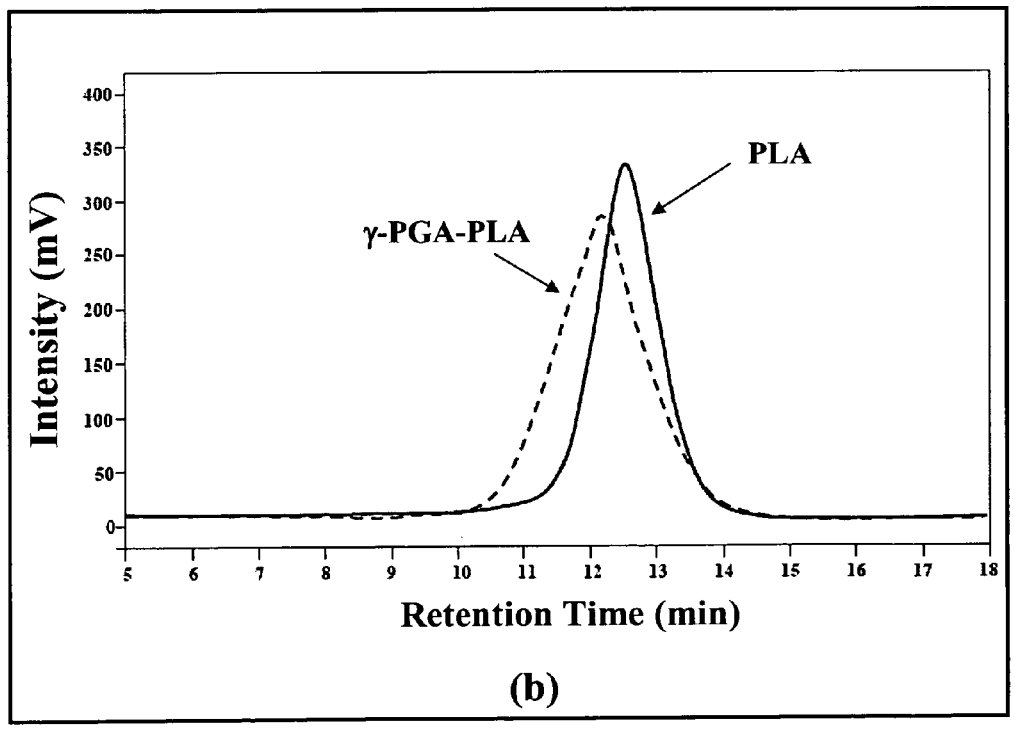

Low-molecular-weight γ-PGA was produced by hydrolyzing the purified γ-PGA obtained from fermentation at 150° C. for distinct durations. Solutions of the purified γ-PGA obtained from fermentation and the hydrolyzed γ-PGA were analyzed by a GPC system. As shown in FIG. 10, the purified γ-PGA obtained from fermentation had a high average molecular weight (Mn ~320 kDa) with a polydispersity of about 1.8. When γ-PGA was hydrolyzed at 150° C. for 5 hours, the average molecular weight of γ-PGA was reduced to about 5 kDa. To reduce the polydispersity of the hydrolyzed γ-PGA, the hydrolyzed γ-PGA (~5 kDa) was further dialyzed twice (using a membrane with MWCO: 3500 and a membrane with MWCO: 6,000-8,000) against deionized water. Thus, obtained γ-PGA had an average molecular weight of about 4 kDa with a polydispersity of 1.3 (FIG. 10). This specific γ-PGA was used subsequently, together with PLA, to synthesize block copolymers to prepare the nanoparticles.

Example No. 14

Synthesis of γ-PGA-PLA Block Copolymers

Block copolymers composed of γ-PGA and PLA were synthesized using CDI to activate the terminal hydroxyl group of PLA (Polymer 1997; 38:6235-6242). CDI (82 mg) was dissolved in 1,4-dioxane (20 ml) in a nitrogen atmosphere and PLA (0.1 g) was subsequently added into the solution. The clear solution was stirred at 37° C. for 2 hours. Afterward, the solution was dialyzed extensively against deionized water at 4° C. Finally, the activated PLA was obtained via centrifugation.

The acidified form of the hydrolyzed γ-PGA (10 mg, Mn ~4 kDa, PDI=1.3) was dissolved in DMSO (5 ml) in a dry, stoppered 20 ml round bottom flask in a nitrogen atmosphere. After dissolution of DMAP (3 mg), a calculated amount of activated PLA (25 mg) was added. The solution was stirred at room temperature for 3 days, after which the reaction was stopped by adding 0.1 ml of concentrated HCl to neutralize DMAP and imidazole. The reaction mixture was transferred to a dialysis tube and dialyzed for 2 days against deionized water at 4° C. Finally, the product (γ-PGA-PLA block copolymers) was lyophilized and stored at −20° C. until used. The molecular weight distribution of the synthesized block copolymers was determined using a GPC system equipped with a Jordi Gel DVB Mixed Bed column (250×10 mm, Jordi Associates, Inc., MA) and a RI detector. Tetrahydrofuran (THF) was used as an elution solvent (1 ml/min) and polystyrene standards for column calibration.

Low-molecular-weight γ-PGA was produced by hydrolyzing the purified γ-PGA obtained from fermentation at 150° C. for distinct durations. Solutions of the purified γ-PGA obtained from fermentation and the hydrolyzed γ-PGA were analyzed by a GPC system. As shown in FIG. 10, the purified γ-PGA obtained from fermentation had a high average molecular weight (Mn ~320 kDa) with a polydispersity of about 1.8. When γ-PGA was hydrolyzed at 150° C. for 5 hours, the average molecular weight of γ-PGA was reduced to about 5 kDa. To reduce the polydispersity of the hydrolyzed γ-PGA, the hydrolyzed γ-PGA (~5 kDa) was further dialyzed twice (using a membrane with MWCO: 3,500 and a membrane with MWCO: 6,000-8,000) against deionized water. Thus, obtained γ-PGA had an average molecular weight of about 4 kDa with a polydispersity of 1.3 (FIG. 10). This specific γ-PGA was used subsequently, together with PLA, to synthesize block copolymers to prepare the nanoparticles.

Example No. 15

Preparation of the Paclitaxel-Loaded Nanoparticles

The paclitaxel-loaded nanoparticles were produced using an emulsion/solvent evaporation technique (Colloid Surface B, 2000; 18:301-313). Briefly, 10 mg of block copolymers were dissolved in 1 ml methylene chloride, and paclitaxel was subsequently added with varying feed weight ratios to block copolymer [paclitaxel/copolymer (P/C)=0.5/10, 1/10, 2/10, and 3/10]. The solution was then stirred for 2 hours at room temperature and was emulsified in 50 ml of a 0.1 wt % sodium cholate solution using a sonicator (VCX-750, Sonics & Materials Inc., Newtown, Conn., cycles of 1 second sonication followed by 1 second of pauses, total time 20 minutes). Afterward, the solvent was evaporated in a vacuum oven at 37° C. for 1 hour. The resulting suspension was filtered through a 0.8-μm membrane filter (Whatman) and then centrifuged for 60 min at 18,000 rpm at 4° C. The supernatant was subsequently discarded and the pellet was resuspended by 10 ml phosphate buffered saline (PBS, pH 7.4, Sigma). The size distribution and zeta potential of the prepared nanoparticles were measured using a Zetasizer (3000HS, Malvern Instruments Ltd., Worcestershire, UK).

TEM and AFM were used to observe the morphology of the paclitaxel-loaded nanoparticles. The TEM sample was prepared by placing a drop of the paclitaxel-loaded nanoparticle solution onto a 400 mesh copper grid coated with carbon. About 2 minutes after deposition, the grid was tapped with a filter paper to remove surface water and negatively stained by using a 2% (by w/v) phosphortungsten acid (PTA) solution. The AFM sample was prepared by casting a drop of the paclitaxel-loaded nanoparticle solution on a slide glass and then dried in vacuum.

Figure 12:
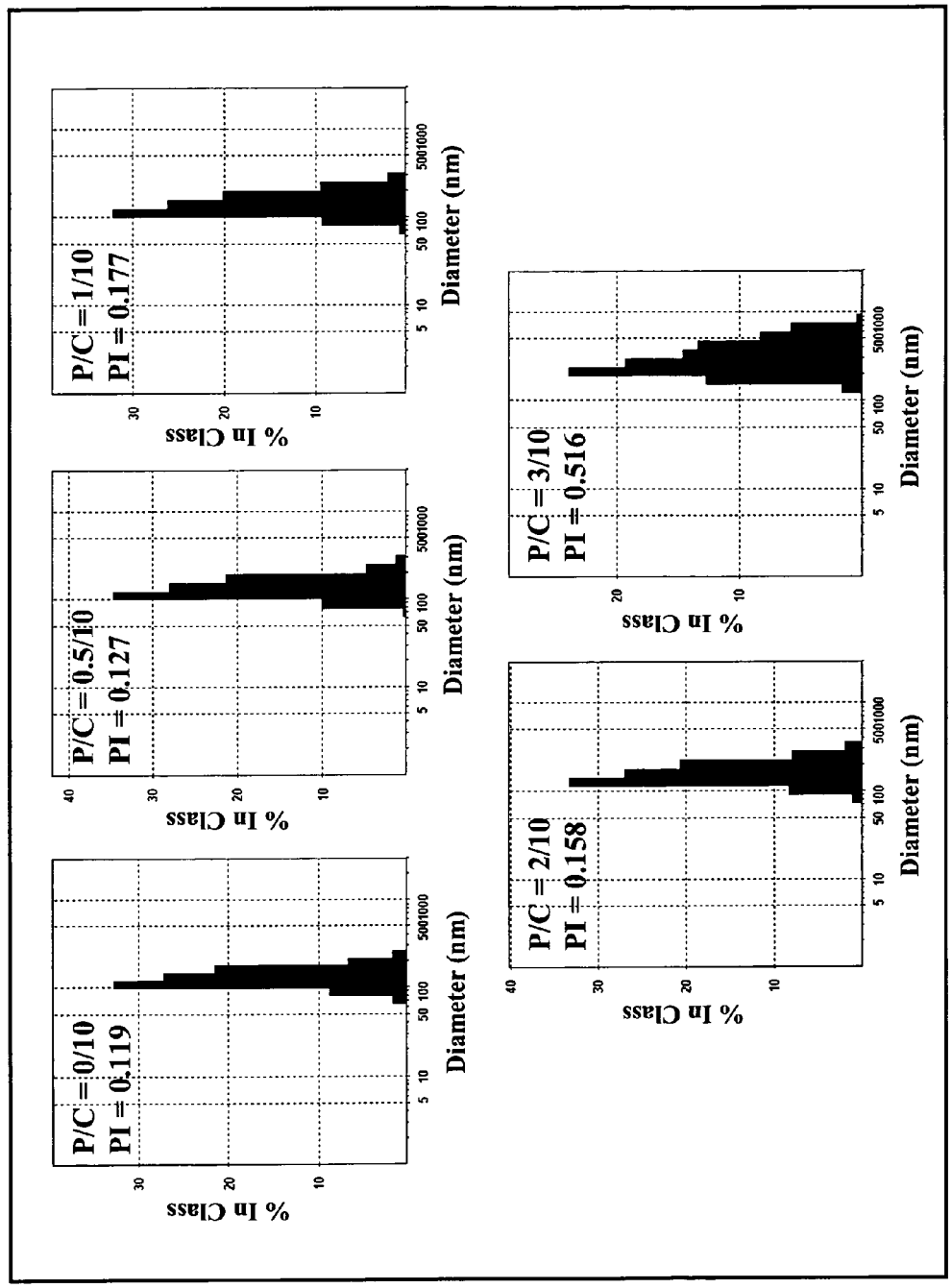
FIG. 12 shows size distributions of the nanoparticles prepared with varying feed weight ratios of paclitaxel to block copolymer (the P/C ratio). PI: the polydispersity index of the size distribution of the prepared nanoparticles.
Figure 13:
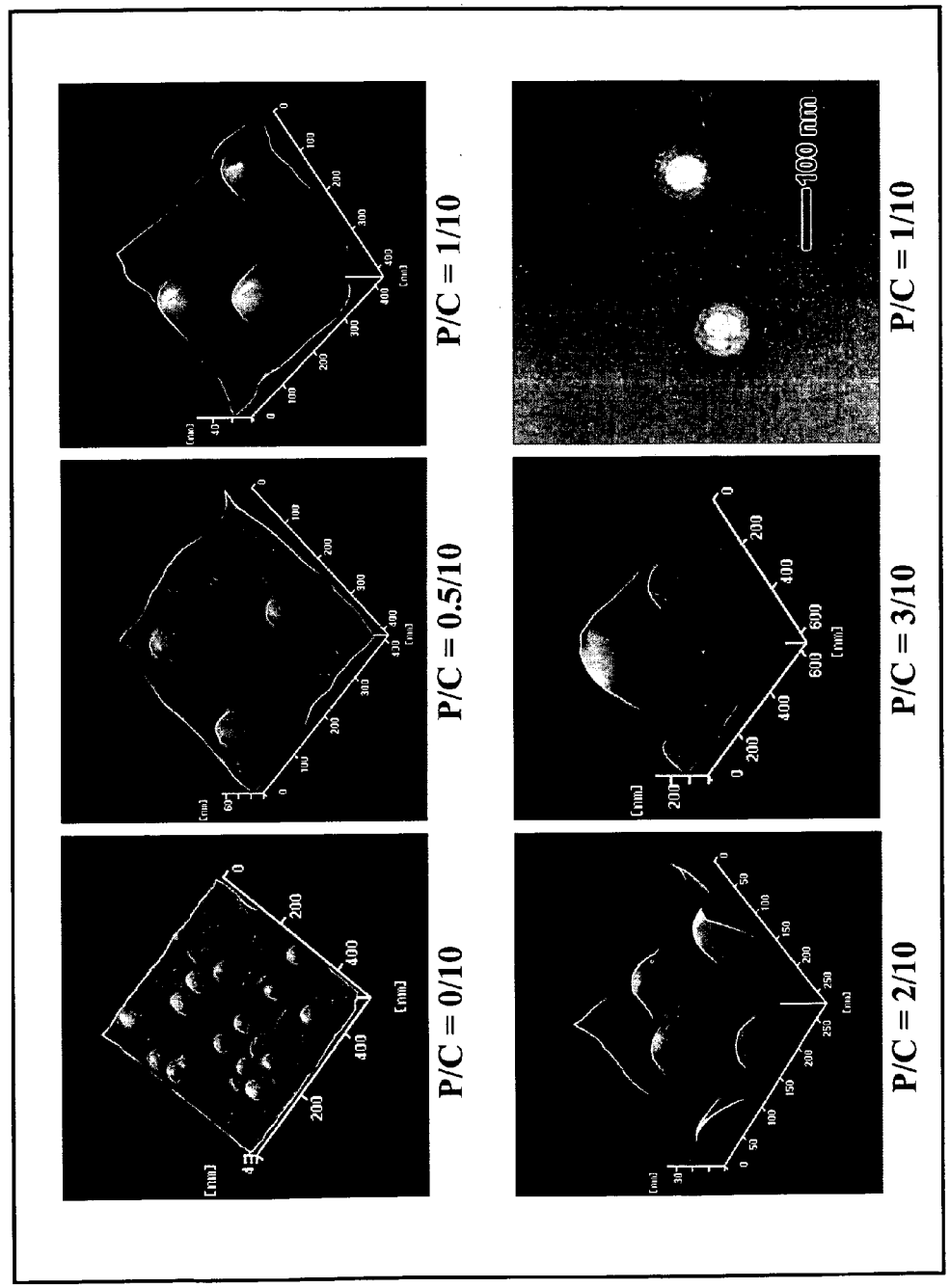
FIG. 13 shows morphology of the nanoparticles prepared with varying feed weight ratios of paclitaxel to block copolymer (the P/C ratio) obtained by the AFM and TEM.

The size distribution and zeta potential of the prepared nanoparticles play important roles in determining their fates after administration. As shown in Table 2, the particle size of the prepared nanoparticles increases significantly with increasing the P/C ratio. Dynamic light scattering measurements further demonstrated that all the prepared nanoparticles have a narrow size distribution, with the exception of those prepared with a P/C ratio of 3/10 (FIG. 12). The AFM and TEM examinations showed that the morphology of all the prepared nanoparticles is spherical in shape with a smooth surface (FIG. 13).

TABLE 2

Particle size, zeta potential, and drug loading content (LC) and loading efficiency (LE) of the nanoparticles prepared with varying feed weight ratios of paclitaxel to block copolymer (the P/C ratio).

| P/C Ratio (n = 4) | Particle Size (nm) | Zeta Potential (mV) | LC (%) | LE (%) |
|---|---|---|---|---|
| 0/10 | 115.4 ± 4.2 | −21.4 ± 2.3 | — | — |
| 0.5/10 | 125.9 ± 5.5 | −22.5 ± 3.2 | 3.7 ± 0.1 | 76.5 ± 2.4 |
| 1/10 | 128.8 ± 3.4 | −19.6 ± 1.8 | 5.1 ± 0.2 | 53.7 ± 1.7 |
| 2/10 | 144.4 ± 2.6 | −20.3 ± 2.7 | 5.8 ± 0.2 | 30.8 ± 2.3 |
| 3/10 | 263.2 ± 6.8 | −19.2 ± 2.2 | 6.1 ± 0.2 | 21.7 ± 4.2 |

Hashida et al. reported that the majority of the fenestrate of the liver sinusoid is usually smaller than 200 nm in diameter (J. Control. Release 1998; 53:301-310). Thus, large particles hardly reach the liver's parenchymal cells. Additionally, drug carriers with a diameter larger than 200 nm are readily scavenged non-specifically by monocytes and the reticuloendothelial system (Biochim. Biophys. Acta, 1994: 1190:99-107). It was reported that smaller particles tended to accumulate at the tumor sites due to the EPR (enhanced permeability and retention) effect (Crit. Rev. Ther. Drug Carrier Syst. 1998; 6:193-210) and a greater internalization was also observed (Adv. Drug Deliver. Rev. 2002; 54:695-713).

As shown in Table 3, the particle size of the Gal-NPs was comparable to that of the NPs (p>0.05). However, the zeta potential of the former was significantly lower than that of the latter (p<0.05). This is because galactosamine was conjugated to the carboxyl (—COO−) groups on γ-PGA (the hydrophilic shell of the nanoparticles) and thus reduced the negative surface charge of the Gal-NPs. The drug loading content and loading efficiency of the Gal-NPs were relatively lower than those of the NPs (p<0.05).

TABLE 3

Particle size, zeta potential, and drug loading content (LC) and loading efficiency (LE) of the paclitaxel-loaded nanoparticles without (NPs) or with (Gal-NPs) galactosamine conjugated.

| Samples (n = 4) | Particle Size (nm) | Zeta Potential (mV) | LC (%) | LE (%) |
|---|---|---|---|---|
| NPs | 128.8 ± 3.4 | −19.6 ± 1.8 | 5.1 ± 0.2 | 53.7 ± 1.6 |
| Gal-NPs | 127.5 ± 2.5 | −10.6 ± 2.0 | 4.8 ± 0.2 | 50.2 ± 2.1 |

It was found that the prepared paclitaxel-loaded nanoparticles have a negative surface charge with a zeta potential of about −20 mV (Table 2), due to the carboxyl (—COO−) groups on the hydrophilic γ-PGA shell. This may affect the cellular uptake of the prepared nanoparticles due to electrostatic repulsion forces between the nanoparticles and the rather negatively charged surface of cells. However, Wakebayashi et al. suggested that introduction of a specific ligand on the nanoparticles may enhance their cellular uptake via a receptor-mediated endocytosis (J. Control. Release 2004; 95:653-664). Additionally, it was reported that positively charged carriers might induce a non-specific interaction with unintended target tissues, particularly under in vivo conditions after administration (J. Control. Release 2004; 95:653-664, Blood 2001; 97:2221-2229).

Example No. 16

Loading Content and Loading Efficiency of the Paclitaxel-Loaded Nanoparticles

The drug loading content and loading efficiency of the nanoparticles were determined using a high-performance liquid chromatography (HPLC) system equipped with a $C_{18}$ analytic column (4.6×250 mm, particle size 5 μm, ThermoQuest, BDS, Runcorn, UK). Two milligrams of the freeze-dried paclitaxel-loaded nanoparticles were dissolved in 1 ml dichloromethane under vigorous vortexing. This solution was dried by evaporating dichloromethane in vacuum and then was dissolved in a mixture of 50/50 (v/v) ethanol and deionized water for the HPLC analysis. The flow rate of the mobile phase (60% acetonitrile and 40% deionized water by v/v), delivered by an HPLC pump (TCP, P-100, Riviera Beach, Fla.), was 1 ml/min at 30° C. The injection volume was 40 μl and paclitaxel eluted from the column was monitored with an UV detector (Jasco 875-UV, Tokyo, Japan) at 227 nm. The drug loading content and loading efficiency of the nanoparticles were calculated using the equations listed below, respectively.

$$\text{Loading Content (\%)} = \frac{\text{weight of paclitaxel in the nanoparticles}}{\text{weight of the nanoparticles}} \times 100\%$$

$$\text{Loading Efficiency (\%)} = \frac{\text{weight of paclitaxel in the nanoparticles}}{\text{weight of the feeding paclitaxel}} \times 100\%$$

Paclitaxel is highly hydrophobic with a solubility of approximately 1 pg/ml in aqueous solution at pH 7.4 (J. Control. Release 2003; 89:437-446). Thus, in the drug loading process, incorporation of paclitaxel in the nanoparticles and precipitation of paclitaxel in aqueous solution competed with each other. With increasing the P/C ratio, incorporation of paclitaxel in the nanoparticles (the drug loading content) appears to increase, while precipitation of paclitaxel in aqueous solution is more pronounced and consequently results in a significantly lower drug loading efficiency (Table 2, $p<0.05$).

Example No. 17

Release of Paclitaxel from the Loaded Nanoparticles

The release profiles of paclitaxel from the prepared nanoparticles were investigated in PBS at 37° C. The freeze-dried paclitaxel-loaded nanoparticles were weighed and resuspended in a centrifuge tube containing 20 ml PBS. The tube was placed in a shaker water bath at 37° C. At particular time intervals, the tube was taken out and centrifuged. The supernatant was poured out, freeze-dried, and then dissolved in a mixture of 50/50 (v/v) ethanol and deionized water for the HPLC analysis. The pellet was resuspended in 20 ml fresh PBS for continuous release measurements. The paclitaxel released at each time point was calculated using a calibration curve (Biomaterials 2004; 25:2843-2849).

Figure 14:
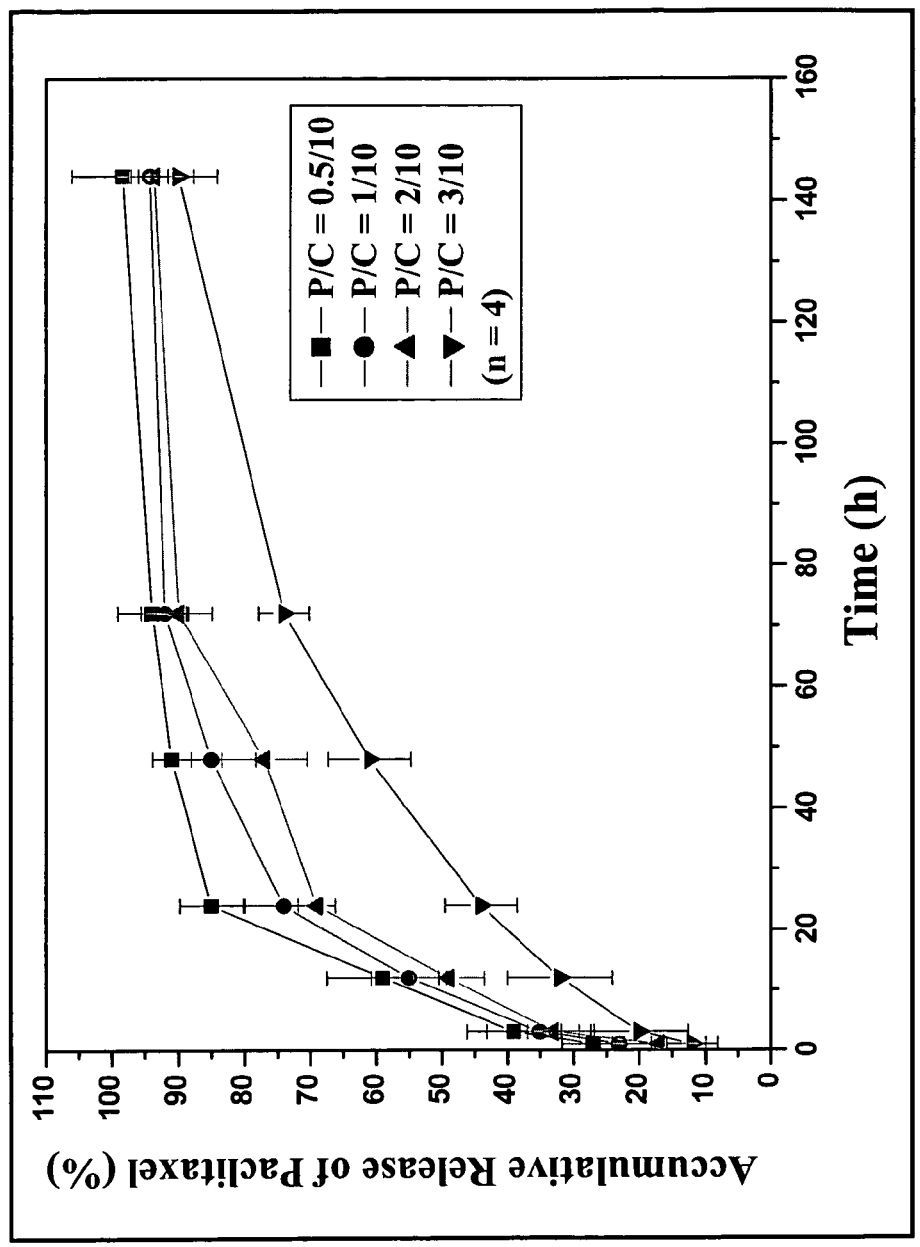
FIG. 14 shows release profiles of paclitaxel from the nanoparticles prepared with varying feed weight ratios of paclitaxel to block copolymer (the P/C ratio).

As shown in FIG. 14, paclitaxel was continuously released from the nanoparticles prepared with distinct P/C ratios. All samples exhibited a burst release of paclitaxel at the initial stage. About 10-25% of the encapsulated drug was released in the first hour. This may be due to some portion of drugs were deposited at the region near the γ-PGA shell of the prepared nanoparticles.

With increasing the P/C ratio, the release rate of paclitaxel from the prepared nanoparticles decreases significantly. It was reported that a hydrophobic drug encapsulated within the nanoparticles partially crystallizes at a higher drug loading content, while it forms a molecular dispersion at a lower drug loading content (Science 1994; 263:1600-1603). The crystallized drug in the hydrophobic core of the nanoparticles is expected to dissolve more gradually and diffuse to their outer aqueous phase more slowly than that in the form of a molecular dispersion. Additionally, it would take a longer time for the encapsulated drug to diffuse across the polymer matrix to the aqueous medium for a larger size of nanoparticles (i.e., with increasing the P/C ratio, see Table 2).

Figure 15:
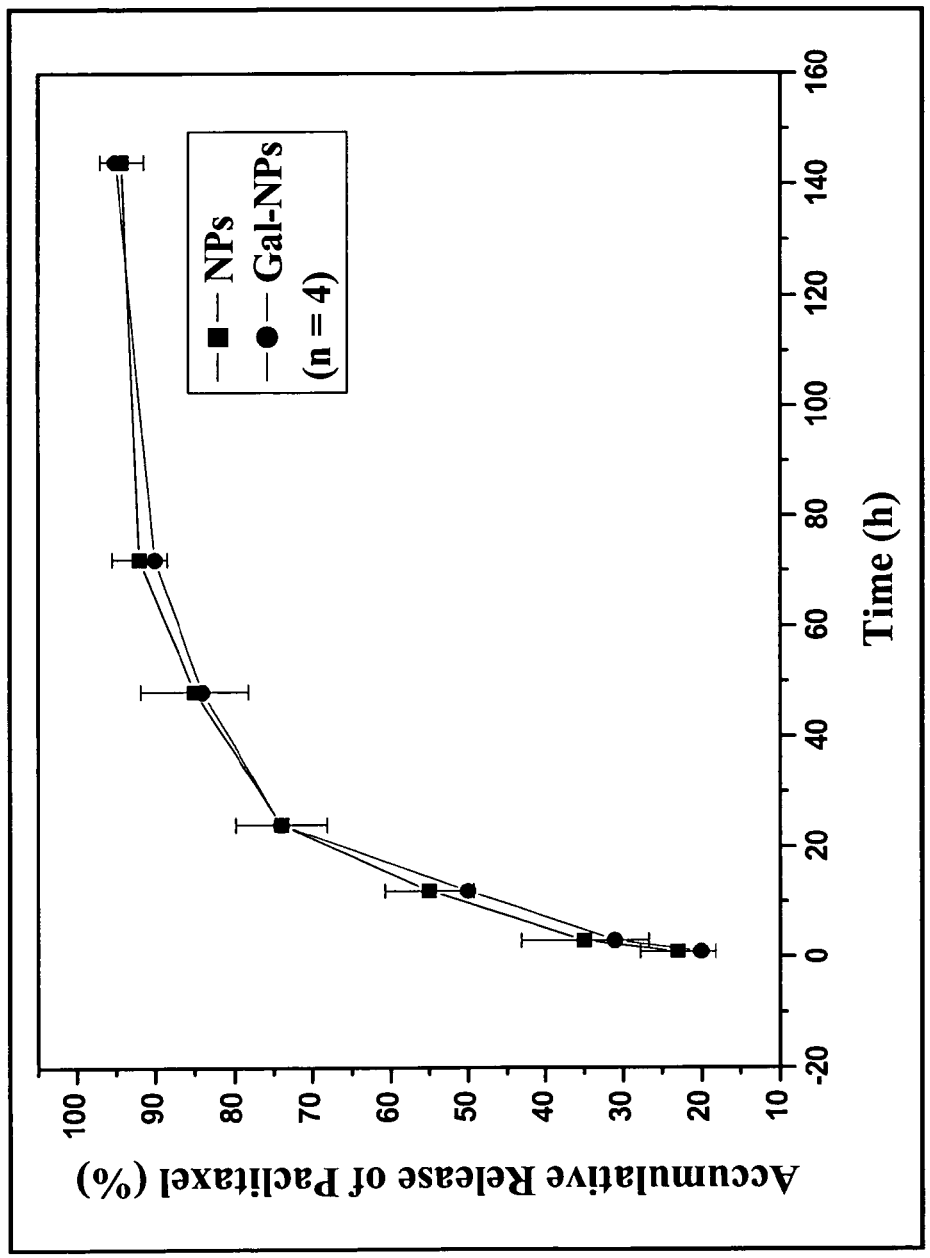
FIG. 15 shows release profiles of paclitaxel from the nanoparticles without (NPs) or with (Gal-NPs) galactosamine conjugated.

As shown in FIG. 15, both the NPs and the Gal-NPs have a similar release profile of paclitaxel ($p>0.05$) and exhibit a burst release of paclitaxel at the initial stage. About 20% of the encapsulated drug in the NPs or the Gal-NPs was released in the first hour. This may be due to some portion of drugs were deposited at the region near the γ-PGA shell of the prepared nanoparticles.

Example No. 18

Conjugation of Galactosamine to the Paclitaxel-Loaded Nanoparticles

Galactosamine was conjugated to the paclitaxel-loaded nanoparticles via an amide linkage by EDC in the presence of NHS (J. Biomed. Mat. Res. 2003; 64A:427-438, J. Appl. Polym. Sci. 2004; 91:4017-4026). The conditions found in our co-pending application U.S. Ser. No. 10/958,864 filed Oct. 5, 2004, to conjugate galactosamine on the nanoparticles that had the greatest amount of nanoparticles internalized in HepG2 cells were used in the present study (J. Control. Release 2005; 105:213-225). The obtained galactosylated nanoparticles were separated from unreacted molecules via ultrafiltration and then lyophilized. The content of galactosamine conjugated on the nanoparticles was determined by the Morgan Elson assay (Bioconjug. Chem. 2001; 12:890-899).

As discussed earlier, with increasing the P/C ratio, the drug loading content of the prepared nanoparticles increases significantly, while their drug loading efficiency decreases remarkably (Table 2). To obtain a comparatively high drug loading content simultaneously with a high loading efficiency (Table 2), the nanoparticles prepared with a P/C ratio of 1/10 (the NPs) were used for the rest of the study. For the potential of targeting liver cancer cells, galactosamine was conjugated to the paclitaxel-loaded nanoparticles (the Gal-NPs). As determined by the Morgan Elson assay, the amount of galactosamine conjugated on the Gal-NPs was 66.2±2.4 nmole/mg nanoparticles (n=4). The particle size of the Gal-NPs (127.5±2.5 nm) was comparable to that of the NPs (128.8±3.4 nm, $p>0.05$). However, the zeta potential of the former (−10.6±2.0 mV) was significantly lower than that of the latter (−19.6±1.8 mV, $p<0.05$). This is because galactosamine was conjugated to the carboxyl ($-COO^-$) groups on γ-PGA and thus reduced the negative surface charge of the Gal-NPs.

Example No. 19

Viability of HepG2 Cells Treated with Distinct Paclitaxel Formulations

The cytotoxicity of the paclitaxel-loaded nanoparticles with or without galactosamine conjugated was evaluated in vitro by the MTT assay, using a clinically available paclitaxel formulation (Phyxol®, Sinphar Pharmaceutical) as a control (J. Biomed. Mater. Res. 2002; 61:360-369). The assay is based on mitochondrial dehydrogenase cell activity as an indicator of cell viability. Briefly, MTT [3-(4,5-dimethyl-thiazol-yl)-2,5-diphenyltetrazolium bromide, Sigma] was dissolved in PBS with a concentration of 5 mg/ml as a stock MTT solution and filtered for sterilization. HepG2 cells were seeded in 24-well plates at $5 \times 10^4$ cells/well and were allowed to adhere overnight. The growth medium was replaced with a fresh one containing varying concentrations (0.25-8 μg/ml) of distinct paclitaxel formulations investigated in the study: Phyxol®, the nanoparticles without galactosamine conjugated (the NPs), and the nanoparticles with galactosamine conjugated (the Gal-NPs).

The cells were then incubated for 3 days and washed twice by 1 ml PBS. Subsequently, the cells were incubated in a growth medium containing 1 mg/ml MTT agent for an additional 4 hours at 37° C. and 500 μl of DMSO was added to each well to ensure solubilization of formazan crystals. Finally, the optical density readings were performed using a multiwell scanning spectrophotometer (MRX Microplate Reader, Dynatech Laboratories Inc., Chantilly, Va.) at a wavelength of 570 nm.

Hepatoma cells are known to recognize galactose- and N-acetylgalactosamine-terminated glycoproteins via the asialoglycoprotein (ASGP) receptors located on their surfaces (Int. J. Pharm. 1999; 188:39-47). It was found in our previous study that in the incubation with the rhodamine-123-containing nanoparticles without galactosamine conjugated, little fluorescence was observed in HepG2 cells on the images taken by the CLSM (J. Control. Release 2005; 105:213-225). This indicated that without galactosamine, only a small amount of the nanoparticles were able to be internalized in cells, due to electrostatic repulsion forces between the nanoparticles and the cells as mentioned earlier. Hence, the NPs prepared in the study released paclitaxel mainly outside of the cells (i.e., in the culture medium). The released paclitaxel was then diffused into HepG2 cells and led to inhibit the growth of the cells. Accordingly, under in vivo conditions after administration, the normal tissues may be non-selectively exposed to paclitaxel released from the NPs in the blood stream, which can lead to unwanted toxic side effects.

In contrast, with increasing the galactosamine content conjugated on the rhodamine-123-containing nanoparticles, the intensity of fluorescence observed in HepG2 cells increases significantly at 30 min after incubation (J. Control. Release 2005; 105:213-225). This indicates that the galactosylated nanoparticles had a specific interaction with HepG2 cells via ligand-receptor (ASGP) recognition. Therefore, the Gal-NPs prepared in the study were first internalized into HepG2 cells via the ASGP receptors, and then released the encapsulated paclitaxel inside cytoplasm to inhibit the growth of the cells. Thus, the active targeting nature of the Gal-NPs may lead to a high degree of selectivity to the hepatic tumor and enhance their cellular uptake, with a consequent decrease in systemic toxicity.

Figure 16:
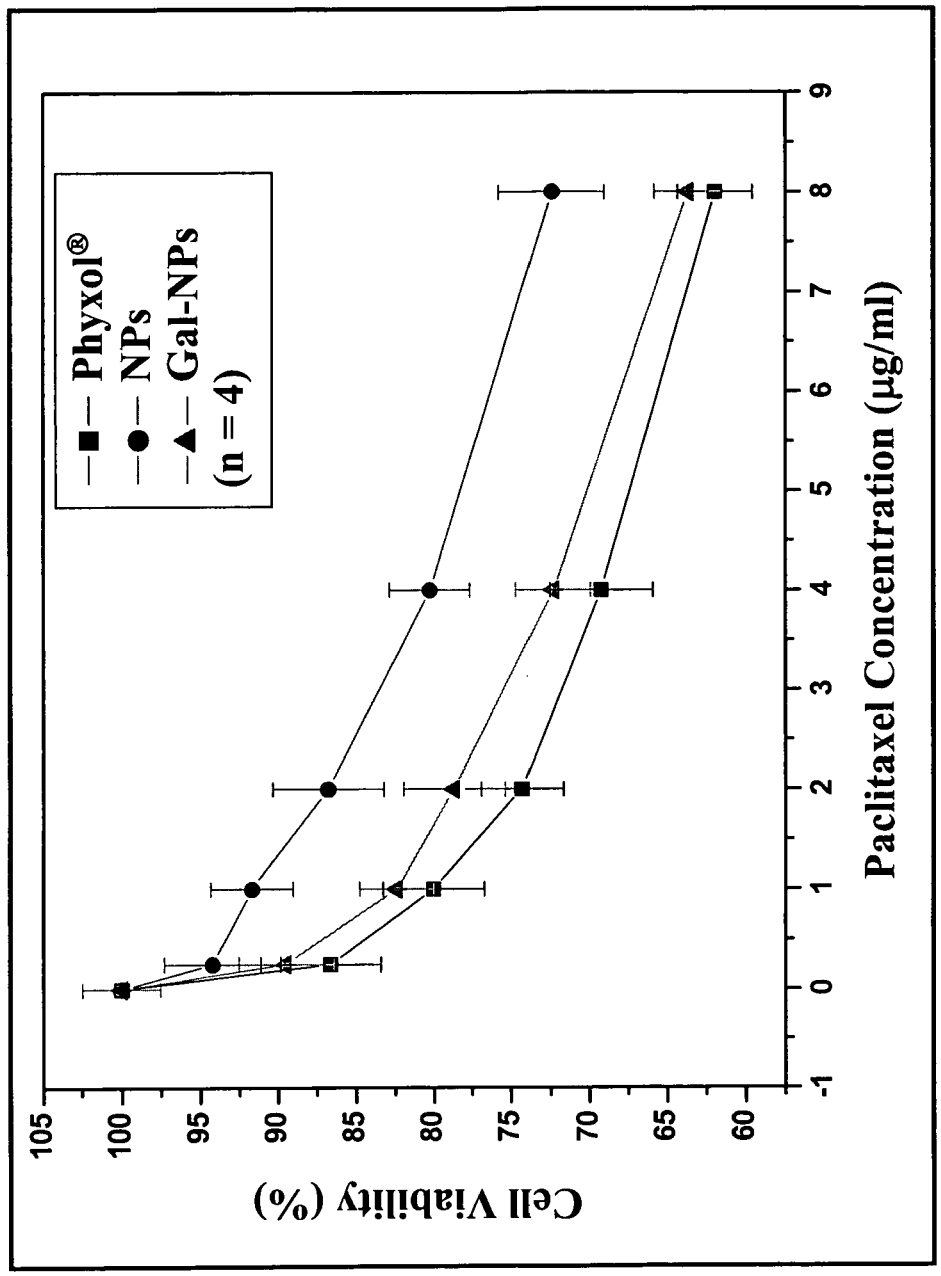
FIG. 16 shows viability of HepG2 cells treated with distinct paclitaxel formulations with varying paclitaxel concentrations. Phyxol®: cells treated with a clinically available paclitaxel formulation (Sinphar Pharmaceutical); NPs: cells treated with the paclitaxel-loaded nanoparticles without galactosamine conjugated; and Gal-NPs: cells treated with the paclitaxel-loaded nanoparticles with galactosamine conjugated.

FIG. 16 shows the viability of HepG2 cells treated with distinct paclitaxel formulations investigated in the study. As shown, the activity in inhibiting the growth of cells by the Gal-NPs was comparable to that of a clinically available paclitaxel formulation (Phyxol®, p>0.05), while the NPs displayed a significantly less activity (p<0.05).

Figure 17A:
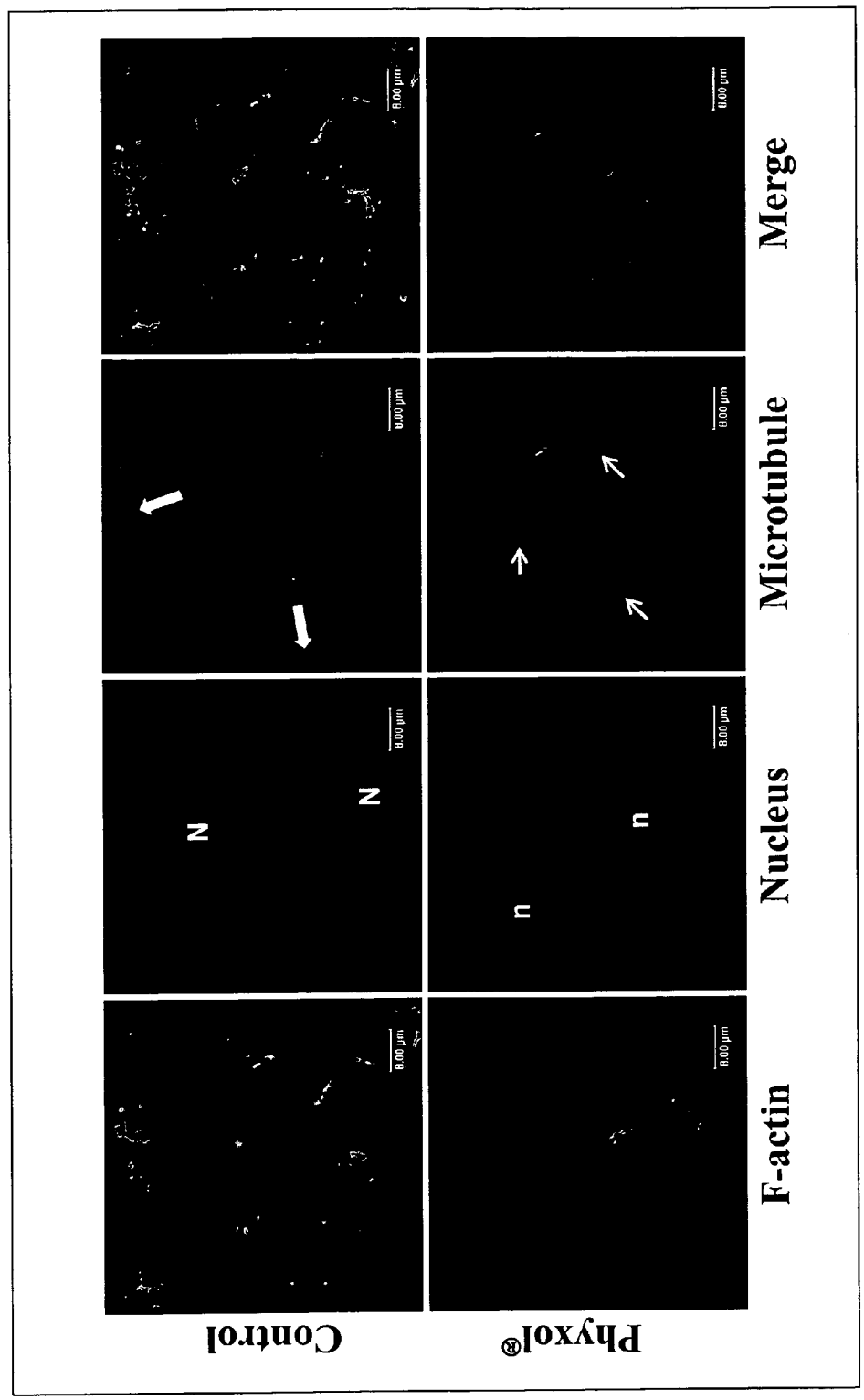
FIG. 17A shows CLSM images of HepG2 cells treated with distinct paclitaxel formulations for 3 days. Control: untreated cells; and Phyxol®: cells treated with a clinically available paclitaxel formulation (Sinphar Pharmaceutical); N: normal nuclei; n: micronuclear formation; ➡: centrosomes; and →: condensation of cytoplasmic microtubules.
Figure 17B:
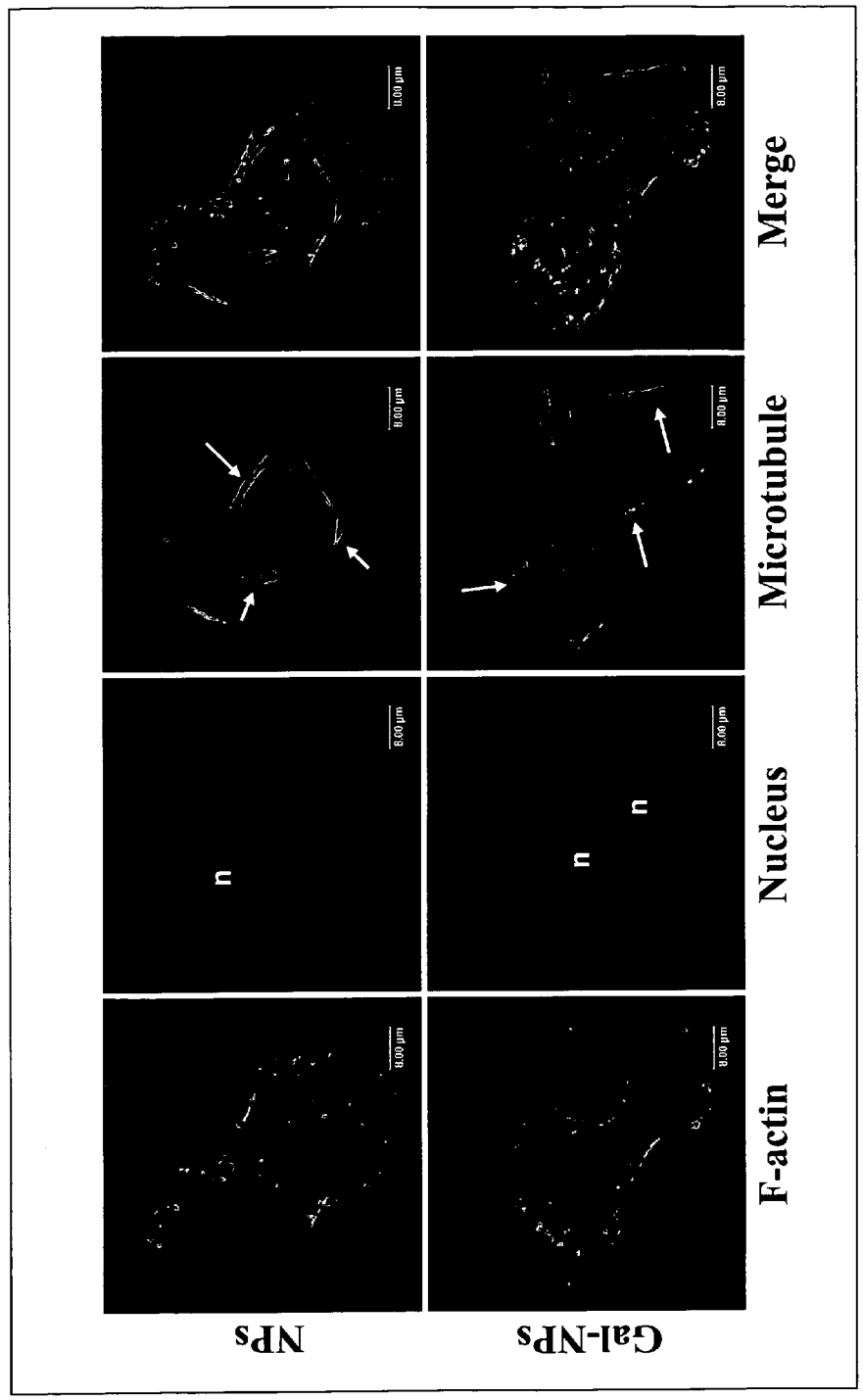
FIG. 17B shows CLSM images of HepG2 cells treated with distinct paclitaxel formulations for 3 days. NPs: cells treated with the paclitaxel-loaded nanoparticles without galactosamine conjugated; and Gal-NPs: cells treated with the paclitaxel-loaded nanoparticles with galactosamine conjugated. N: normal nuclei; n: micronuclear formation; ➡: centrosomes; and →: condensation of cytoplasmic microtubules.

FIG. 17 shows the CLSM images of HepG2 cells treated with Phyxol®, the NPs, or the Gal-NPs. As shown, the untreated HepG2 cells (control) demonstrate normal nuclei, centrosomes, and microtubule networks. In contrast, HepG2 cells exposed to Phyxol®, the NPs, or the Gal-NPs show a significant disruption of the polar spindle of cells and a characteristic condensation of cytoplasmic microtubules. Additionally, micronuclear formation, resulting from improper mitotic spindle assembly, is apparent.

Figure 18:
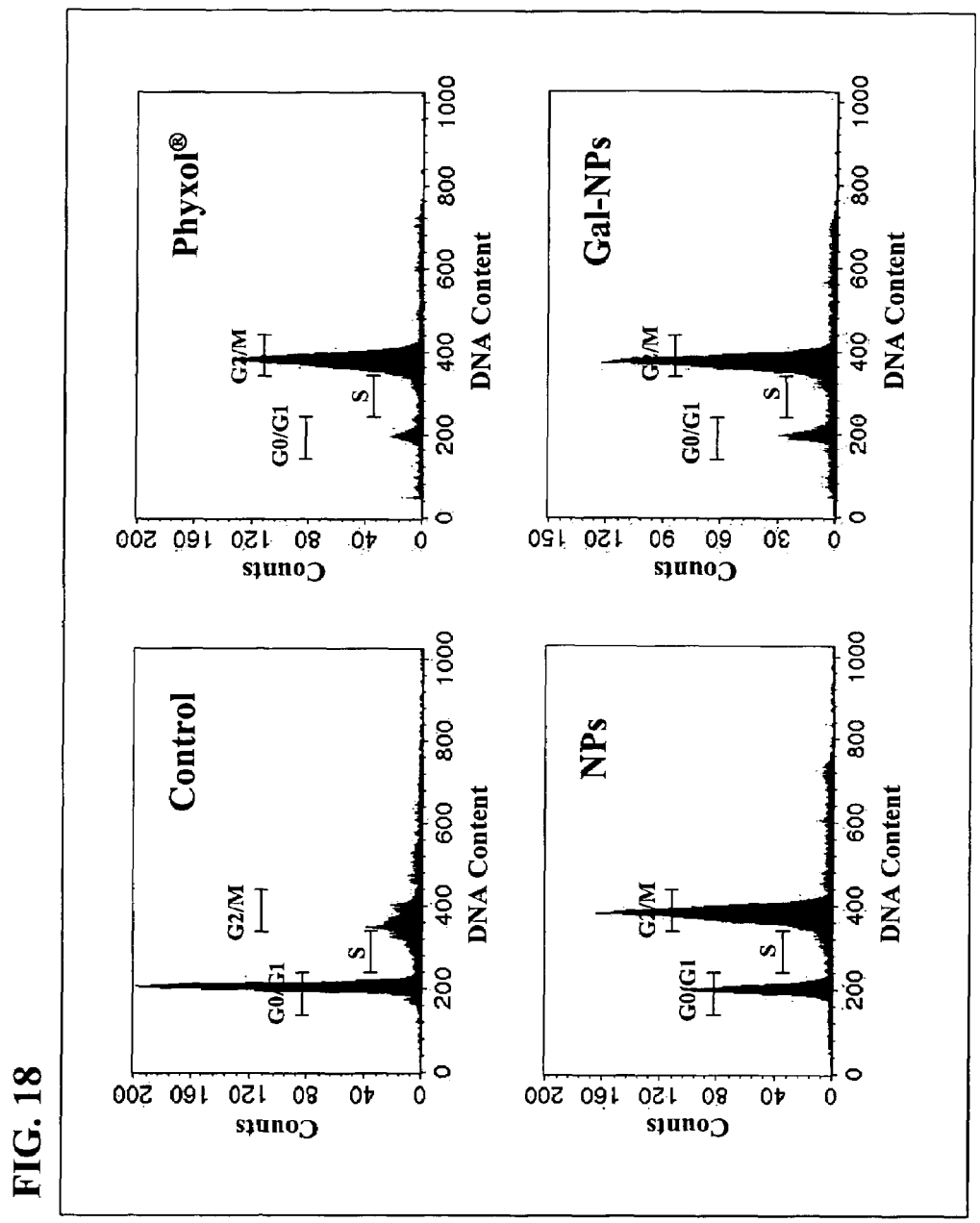
FIG. 18 shows analysis of DNA content in the cell cycle of HepG2 cells treated with distinct paclitaxel formulations for 3 days using a flow cytometer. Control: untreated cells; Phyxol®: cells treated with a clinically available paclitaxel formulation (Sinphar Pharmaceutical); NPs: cells treated with the paclitaxel-loaded nanoparticles without galactosamine conjugated; and Gal-NPs: cells treated with the paclitaxel-loaded nanoparticles with galactosamine conjugated.

As shown in FIG. 18, HepG2 cells treated with distinct paclitaxel formulations result in arrest in the G2/M phase. The arrest of cells in the G2/M phase is highly suggestive of interferences by paclitaxel with spindle formation, and is consistent with our morphological findings observed in FIG. 17. As compared to the untreated cells (control), the sharp peak at the G0/G1 phase was markedly attenuated and was instead mostly in the G2/M phase for the cells treated with Phyxol® or the Gal-NPs. In contrast, for those cells treated with the NPs, this observation was less significant (p<0.05). This again might be attributed to the fact that the NPs lack the property of active targeting to HepG2 cells, as compared to the Gal-NPs.

Example No. 20

Immunofluorescence Analysis of HepG2 cells Treated with Distinct Paclitaxel Formulations HepG2 cells were grown on glass coverslips and then treated with distinct paclitaxel formulations with a final paclitaxel concentration of 8 µg/ml. After incubation for 3 days, the cells were fixed with 3.7% formaldehyde in PBS for 10 min at room temperature and then permeabilized in 0.1% Triton X-100 in PBS containing 1% bovine serum albumin (PBS-BSA) and RNase 100 µg/ml. After washing 3 times with PBS-BSA, the cells were treated with Oregon Green® 514 palloidin (1:100 v/v, Molecular Probes) in PBS-BSA for 20 min. Cells were then incubated for 60 min with anti-bovine α-tubulin mouse mAb (1 µg/ml, Molecular Probes) in PBS-BSA. The Alexa Fluor® 633-conjugated goat anti-mouse IgG antibody (2 µg/ml, Molecular Probes) was added and incubated for another 60 min. Subsequently, cells were rinsed 3 times with PBS-BSA and treated with 100 nM propidium iodide (PI, Sigma) for 5 min.

Before mounting the samples for the CLSM examinations, cells were washed again with PBS and deionized water. Oregon Green® 514 palloidin, PI, or Alexa Fluor® 633 stainings were visualized with excitations at 488, 543, and 633 rn, respectively, using an inversed CLSM (TCS SL, Leica, Germany). Superimposed images were performed with an LCS Lite software (version 2.0).

Example No. 21

Altered Cycling States of HepG2 Cells Treated with Distinct Paclitaxel Formulations To demonstrate whether paclitaxel released from the prepared NPs or the Gal-NPs could restrict HepG2 cells in specific cell cycle stages, flow cytrometric studies were performed. HepG2 cells treated with distinct paclitaxel formulations with a final paclitaxel concentration of 1 µg/ml for 3 days were pelleted at 1500 rpm for 5 min and then were resuspended in PBS. The cell suspension was then added with 100% methanol precooled to −20° C. for 15 min and centrifuged at 1500 rpm for 5 min. The supernatant was discarded, and the cell pellet was rehydrated with PBS. The pellet was stained with a DNA staining solution (10 pg/ml PI and 1 mg/ml RNase A) for 45 min. The DNA content of each cell was measured using a Becton Dickinson FACSCalibur flow cytometer (San Jose, Calif.).

Some aspects of the invention relate to the paclitaxel-loaded nanoparticles with galactosamine conjugated that are configured to be internalized into HepG2 cells via a receptor-mediated endocytosis, resulting in the inhibition of the growth of cells. Therefore in one embodiment, the prepared nanoparticles are provided as a potential drug delivery system for the targeted delivery to liver cancers.

Example No. 22

Study Animals

Male Balb/c mice (5-7 weeks old, 18-22 g) and Balb/c-nu/nu nude mice (5-7 weeks old, 16-20 g) were obtained from the National Laboratory Animal Center (Taipei, Taiwan) and acclimatized for 7 days after arrival. Nude mice were housed in individually ventilated cages (IVC cages) of isolated ventilation to avoid microbial contamination. Balb/c-nu/nu nude mice were injected subcutaneously in the right flank with 0.1 ml of cell suspension containing $10^6$ human hepatoma cells (HepG2) and allowed to grow to a mean volume of 50 mm$^3$ (36). Animal care and use was performed in compliance with the "Guide for the Care and Use of Laboratory Animals" prepared by the Institute of Laboratory Animal Resources, National Research Council, and published by the National Academy Press, revised 1996.

Example No. 23

Biodistribution of the Prepared Nanoparticles

In the study, rhodamine-123 was used as a model fluorescent probe that can be encapsulated in the hydrophobic core of the prepared nanoparticles (J. Control. Release 2005; 105:213-225). The prepared rhodamine-123-containing nanoparticles in PBS were injected into the tail vein of normal or tumor-bearing mice at a dose of 10 mg/kg. At different time intervals after injection, mice were sacrificed, blood was drawn, and various tissues such as the brain, liver, spleen, lung, kidney, and tumor were excised. An aqueous solution (10 ml) containing deionized water and ethanol (50/50 by v/v) was added to each tissue, and the mixture was homogenized. The mixtures were subsequently centrifuged at 14,000 rpm for 30 min. The supernatants were then lyophilized and resuspended in 1 ml deionized water. Finally, the fluorescence intensities of the solutions were measured using a spectrofluorometer (F-2500, Hitachi, Tokyo, Japan) at an emission wavelength of 520 nm and an excitation wavelength of 490 nm (J Control Release 2003; 91:135-145).

Figure 19:
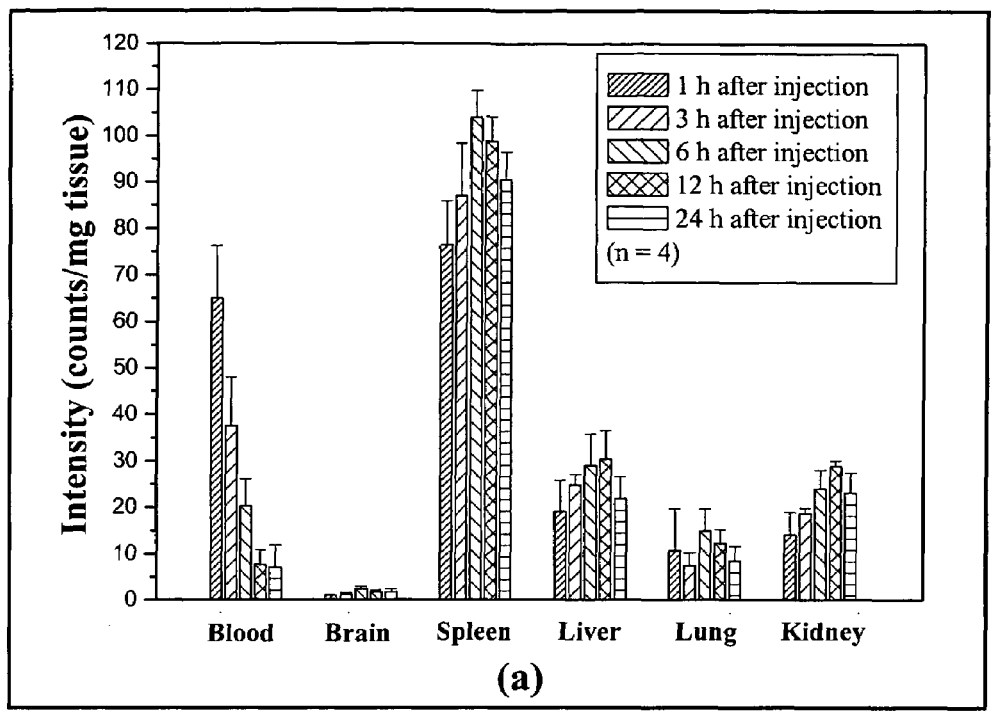
FIG. 19 shows biodistributions of the nanoparticles loaded with rhodamine 123 (a) without galactosamine conjugated (the NPs) and (b) with galactosamine conjugated (the Gal-NPs) in normal mice.
Figure 19:
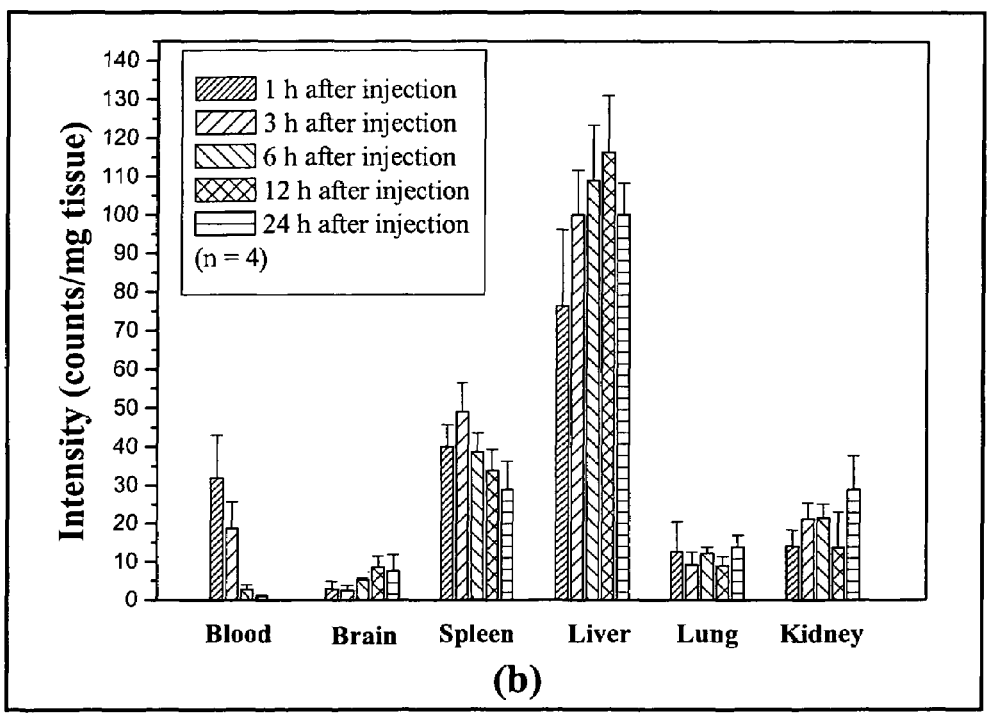

Biodistributions of the prepared nanoparticles in various organs in normal mice and hepatoma-tumor-bearing nude mice were evaluated at distinct durations after the injection of the NPs or the Gal-NPs loaded with rhodamine 123. For normal mice, the NPs were distributed mainly in the spleen (FIG. 19a) due to the splenic filtration (20), whereas the amount of the Gal-NPs observed in the spleen decreased significantly ($p<0.05$, FIG. 19b). It was found that the Gal-NPs are mainly accumulated in the liver.

Figure 20:
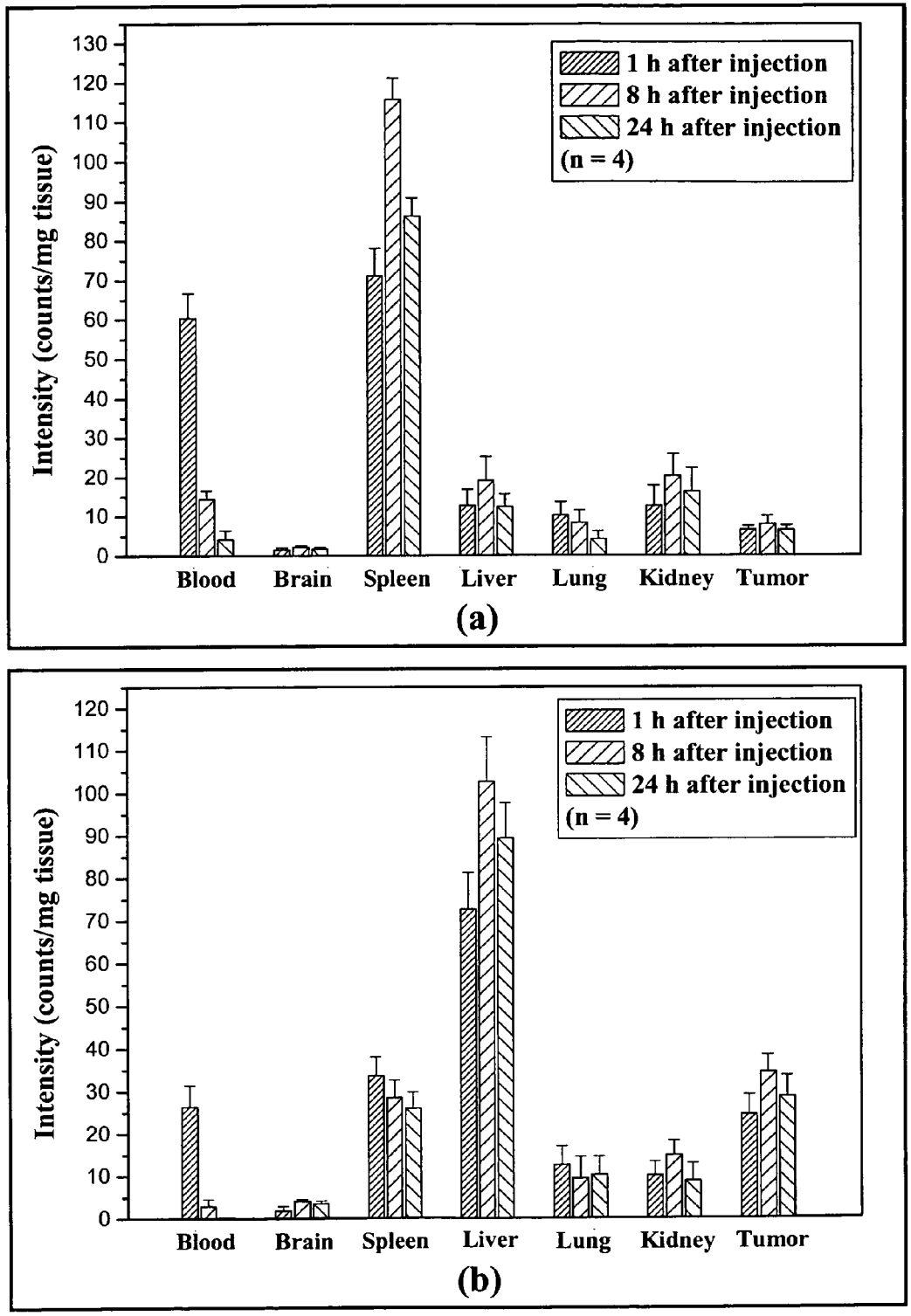
FIG. 20 shows biodistributions of the nanoparticles loaded with rhodamine 123 (a) without galactosamine conjugated (the NPs) and (b) with galactosamine conjugated (the Gal-NPs) in hepatoma-tumor-bearing nude mice.

For hepatoma-tumor-bearing nude mice, similar observations were observed in the spleen and the liver for the groups injected with the NPs (FIG. 20a) or the Gal-NPs (FIG. 20b). It should be noted that the amount of nanoparticles observed at the tumor site for the group injected with the Gal-NPs was significantly greater than that injected with the NPs $p<0.05$).

Figure 21:
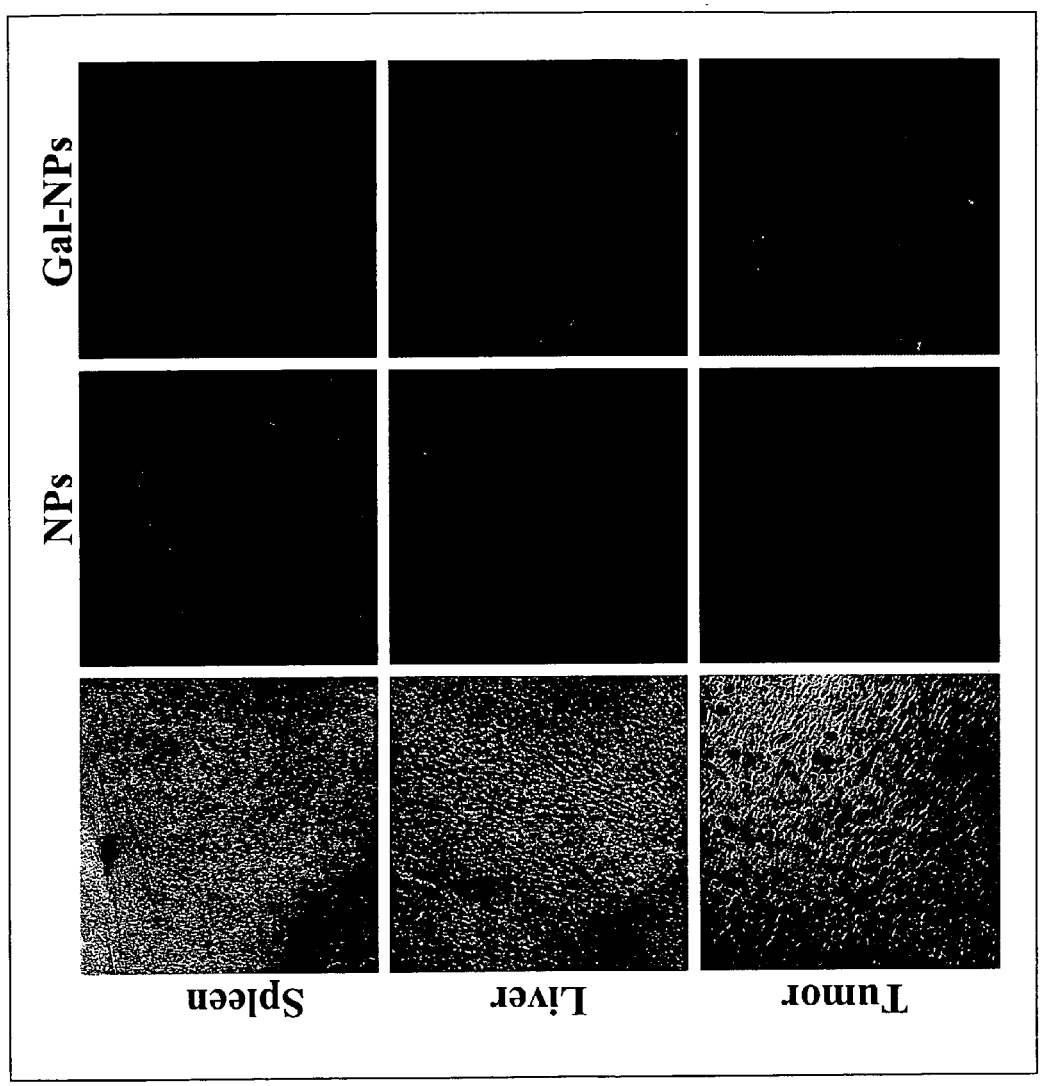
FIG. 21 shows sections of the spleen, liver, and tumor retrieved from the hepatoma-tumor-bearing nude mice injected with the nanoparticles loaded with rhodamine 123 examined by a CLSM. NPs: the group injected with the nanoparticles without galactosamine conjugated; and Gal-NPs: the group injected with the nanoparticles with galactosamine conjugated.

These observations were further confirmed by our CLSM inspection of the spleen, liver, and tumor sections retrieved from the mice injected with the NPs or the Gal-NPs loaded with rhodamine 123 (FIG. 21). For the group injected with the NPs, the intensity of fluorescence observed in the spleen was much stronger than in the liver and the tumor site. In contrast, for the group injected with the Gal-NPs, the intensities of fluorescence observed in the liver and the tumor site increased significantly. The aforementioned results indicated that the galactosylated nanoparticles prepared in the study had a specific interaction with liver's parenchymal cells and HepG2 tumor cells via ligand-receptor recognition.

Example No. 24

Anti-Tumor Efficacy of the Prepared Nanoparticles

The anti-tumor efficacy of distinct paclitaxel formulations against the subcutaneously implanted solid tumors induced by HepG2 cells in nude mice was evaluated. Treatments were started when the tumors in nude mice reached a tumor volume of 50 mm³ and this day was designated day 0. Mice were divided into four different groups [treated with PBS (control), Phyxol®, the NPs, or the Gal-NPs], consisting of four mice in each group. Distinct paclitaxel formulations were then injected via tail vein administration at a single dose of 20 mg paclitaxel/kg in PBS on days 0, 4, 8, 12, 16. The size of the tumor and the change of body weight of each mouse were recorded (J Control Release 2001; 72:191-202, J Control Release 2004; 99:83-101.)

Figure 22:
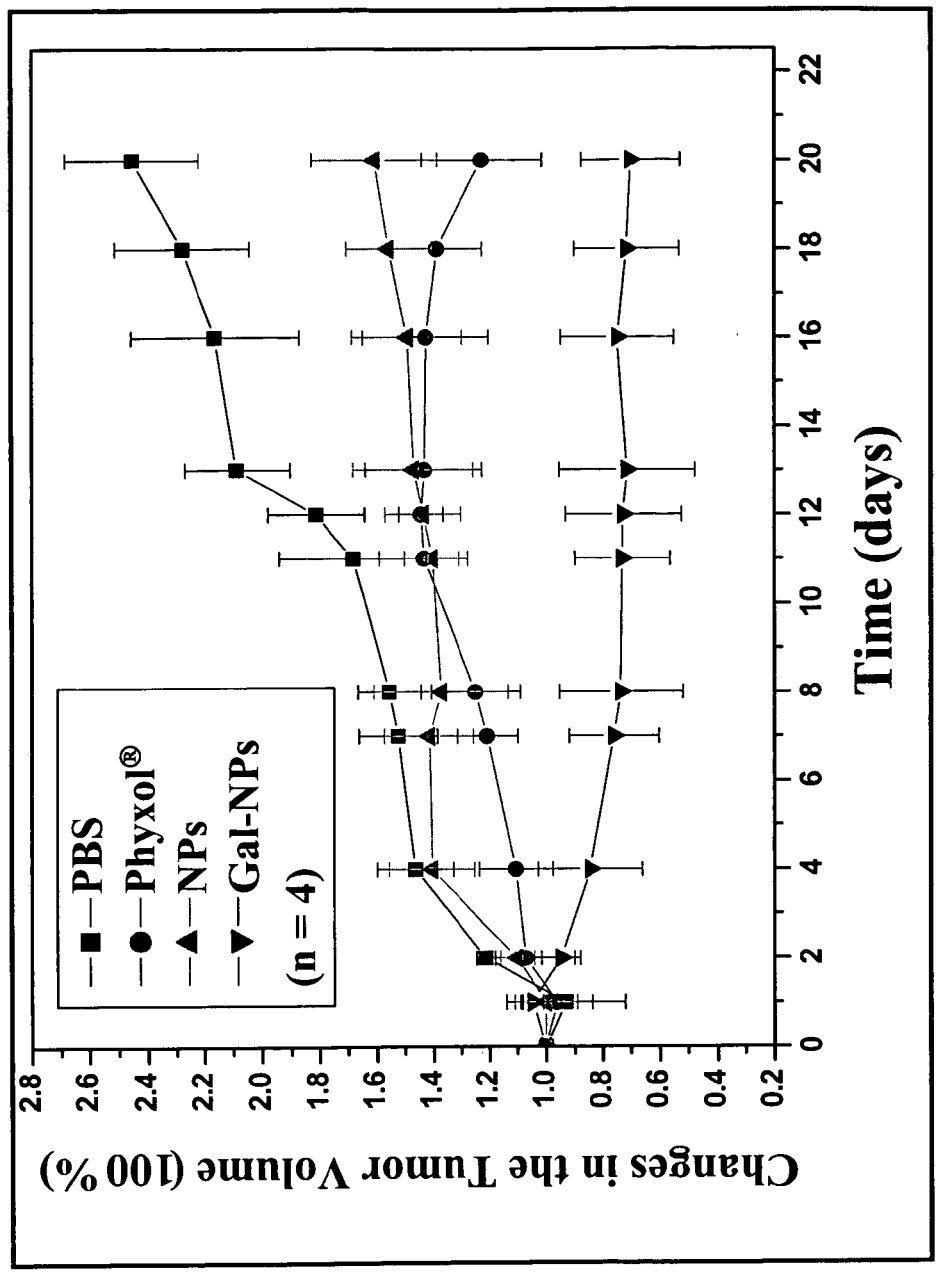
FIG. 22 shows changes in the tumor volume of the hepatoma-tumor-bearing nude mice injected with distinct paclitaxel formulations. PBS: mice injected with PBS; Phyxol®: mice injected with a clinically available paclitaxel formulation (Sinphar Pharmaceutical); NPs: mice injected with the paclitaxel-loaded nanoparticles without galactosamine conjugated; and Gal-NPs: mice injected with the paclitaxel-loaded nanoparticles with galactosamine conjugated.

The anti-tumor efficacy of the NPs and the Gal-NPs was studied in hepatoma-tumor-bearing nude mice. FIG. 22 shows the progress of the tumor growth observed for 20 days in nude mice injected with PBS (control) or distinct paclitaxel formulations. It was found that the size of the tumor for the control group increases significantly with time, indicating that PBS has no significant effect in preventing the tumor growth. In contrast, the groups injected with Phyxol®, the NPs or the Gal-NPs significantly delayed the tumor growth as compared to the control group ($p<0.05$). Among all study groups, the group injected with the Gal-NPs appears to have the most significant efficacy in the reduction of the size of the tumor ($p<0.05$). This is because a large number of the Gal-NPs actively targets at the tumor site as mentioned earlier (FIG. 20b and FIG. 21), and subsequently release their encapsulated paclitaxel to inhibit the growth of the tumor.

Figure 23:
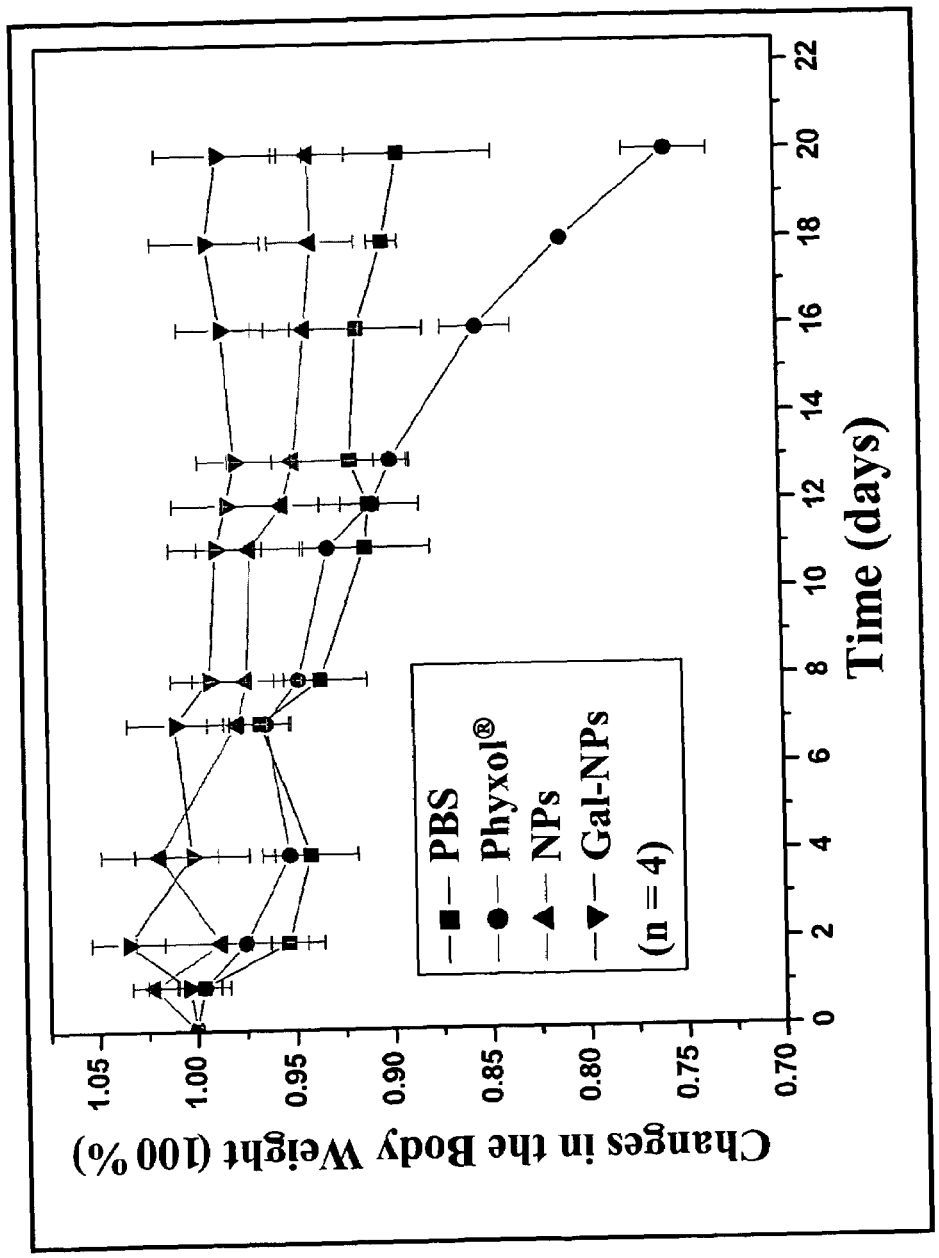
FIG. 23 shows changes in the body weight of the hepatoma-tumor-bearing nude mice injected with distinct paclitaxel formulations. PBS: mice injected with PBS; Phyxol®: mice injected with a clinically available paclitaxel formulation (Sinphar Pharmaceutical); NPs: mice injected with the paclitaxel-loaded nanoparticles without galactosamine conjugated; and Gal-NPs: mice injected with the paclitaxel-loaded nanoparticles with galactosamine conjugated.

As shown in FIG. 23, some weight loss was observed with time for all study groups, with the exception of the group injected with the Gal-NPs ($p>0.05$). The observation of weight loss was particularly remarkable for the group injected with Phyxol® ($p<0.05$). These observations implied that for the group injected with Phyxol® (a free form of paclitaxel), paclitaxel is delivered not only to the tumor cells but also to other normal cells in nude mice, whereas the Gal-NPs are mainly accumulated at the tumor site and the liver.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A method of treating liver cancer in an animal comprising administering a dose of a pharmaceutical composition of nanoparticles to the animals, wherein said nanoparticles comprise γ-PGA-PLA block copolymers that are conjugated with galactosamine.

2. The method of claim 1, wherein said galactosamine containing nanoparticles have a weight ratio of the galactosamine to the nanoparticles at between about 10:1 and 2.5:1.

3. The method of claim 1, wherein at least a portion of the galactosamine containing nanoparticles is loaded with at least one anticancer drug.

4. The method of claim 3, wherein said galactosamine containing nanoparticles have a negative surface charge.

5. The method of claim 1, wherein the nanoparticles are loaded with pharmaceutically active doxorubicin.

6. The method of claim 1, wherein the nanoparticles are loaded with pharmaceutically active.

7. The method of claim 1, wherein at least a portion of the nanoparticles comprises a hydrophobic inner core.

8. The method of claim 1, wherein at least a portion of the nanoparticles comprises a hydrophilic outer shell.

9. The method of claim 1, wherein a mean particle size of the nanoparticles in a solution is in the range of about 50 to 400 nm.

10. The method of claim 1, wherein a mean particle size of the nanoparticles in a solution is in the range of about 10 to 200 nm.

11. The method of claim 1, wherein a therapeutically effective amount of said nanoparticles for treating the liver cancer has an average particulate concentration of the nanoparticles of 50 μg/ml in a solution.

12. The method of claim 1, wherein said galactosamine containing nanoparticles have a galactosamine content of at least 19 nmol/mg nanoparticles.

13. The method of claim 1, wherein γ-FGA component prior to forming the γ-PGA-PLA block copolymers has a molecular weight of about 4 kDa with a polydispersity index of about 1.3.

14. The method of claim 1, wherein at least a portion of the nanoparticles comprises a hydrophobic outer shell.

15. The method of claim 1, wherein said nanoparticles have a surface zeta potential of about −20 mV or higher.

16. The method of claim 1, wherein said nanoparticles are adapted for delivery to a blood vessel of the animal for treating the liver cancer.

17. The method of claim 1, wherein said nanoparticles are adapted for intravenous injection for treating the liver cancer in the animal.

18. The method of claim 1, wherein the γ-PGA-PLA block copolymers are synthesized via a simple coupling reaction process between γ-PGA polymers and PLA polymers.

19. The method of claim 3, wherein the at least one anticancer drug is paclitaxel.

20. The method of claim 3, wherein the at least one anticancer drug is paclitaxel with a loading content of at least 4.0%.

* * * * *